(12) United States Patent
Markland et al.

(10) Patent No.: US 9,090,737 B2
(45) Date of Patent: Jul. 28, 2015

(54) VISCOUS TERPOLYMERS AS DRUG DELIVERY PLATFORM

(75) Inventors: Peter Markland, Birmingham, AL (US); Howard Bowman, Birmingham, AL (US)

(73) Assignee: SurModics, Inc., Eden Prairie, MN (US)

( * ) Notice: Subject to any disclaimer, the term of this patent is extended or adjusted under 35 U.S.C. 154(b) by 642 days.

(21) Appl. No.: 12/269,135

(22) Filed: Nov. 12, 2008

(65) Prior Publication Data

US 2009/0124535 A1     May 14, 2009

Related U.S. Application Data

(60) Provisional application No. 60/987,648, filed on Nov. 13, 2007.

(51) Int. Cl.

| | | |
|---|---|---|
| *C08G 63/08* | (2006.01) | |
| *A61K 9/00* | (2006.01) | |
| *C08G 63/664* | (2006.01) | |
| *A61K 31/7088* | (2006.01) | |
| *A61K 47/02* | (2006.01) | |
| *A61K 47/10* | (2006.01) | |
| *A61K 47/34* | (2006.01) | |
| *A61K 47/36* | (2006.01) | |

(52) U.S. Cl.
CPC .............. *C08G 63/08* (2013.01); *A61K 9/0019* (2013.01); *A61K 31/7088* (2013.01); *A61K 47/02* (2013.01); *A61K 47/10* (2013.01); *A61K 47/34* (2013.01); *A61K 47/36* (2013.01); *C08G 63/664* (2013.01); *C08G 2261/126* (2013.01)

(58) Field of Classification Search
None
See application file for complete search history.

(56) References Cited

U.S. PATENT DOCUMENTS

| | | | |
|---|---|---|---|
| 4,020,558 A | 5/1977 | Cournut et al. | |
| 4,241,489 A | 12/1980 | Manning | |
| 4,595,713 A | 6/1986 | St. John | |
| 4,704,692 A | 11/1987 | Ladner | |
| 4,804,691 A | 2/1989 | English et al. | |
| 4,874,612 A | 10/1989 | Deasy | |
| 4,892,736 A | 1/1990 | Goodson | |
| 4,898,734 A | 2/1990 | Mathiowitz et al. | |
| 5,004,602 A | 4/1991 | Hutchinson | |
| 5,076,807 A | 12/1991 | Bezwada et al. | |
| 5,278,201 A | 1/1994 | Dunn et al. | |
| 5,281,354 A | 1/1994 | Faber | |
| 5,407,609 A | 4/1995 | Tice et al. | |
| 5,468,253 A | 11/1995 | Bezwada et al. | |
| 5,496,605 A | 3/1996 | Augst et al. | |
| 5,514,378 A | 5/1996 | Mikos et al. | |
| 5,558,877 A | 9/1996 | Matlin et al. | |
| 5,568,866 A | 10/1996 | Grosskopf et al. | |
| 5,599,552 A | 2/1997 | Dunn et al. | 424/423 |
| 5,599,852 A * | 2/1997 | Scopelianos et al. | 523/105 |
| 5,665,477 A | 9/1997 | Meathrel et al. | |
| 5,702,716 A | 12/1997 | Dunn et al. | |
| 5,702,717 A * | 12/1997 | Cha et al. | 424/425 |
| 5,739,176 A | 4/1998 | Dunn et al. | |
| 5,759,563 A | 6/1998 | Yewey et al. | |
| 5,853,876 A | 12/1998 | Takano et al. | |
| 5,876,452 A | 3/1999 | Athanasiou et al. | |
| 5,945,115 A | 8/1999 | Dunn et al. | |
| 6,006,122 A | 12/1999 | Smits | |
| 6,086,526 A | 7/2000 | Franischelli | |
| 6,126,919 A | 10/2000 | Stefely et al. | |
| 6,130,200 A | 10/2000 | Brodbeck et al. | |
| 6,149,614 A | 11/2000 | Dunshee et al. | |
| 6,224,622 B1 * | 5/2001 | Kotzev | 606/214 |
| 6,324,435 B1 | 11/2001 | Shchervinsky et al. | |
| 6,331,311 B1 | 12/2001 | Brodbeck et al. | |
| 6,338,859 B1 | 1/2002 | Leroux et al. | |
| 6,406,745 B1 | 6/2002 | Talton | |
| 6,413,536 B1 | 7/2002 | Gibson et al. | |
| 6,432,438 B1 * | 8/2002 | Shukla | 424/426 |
| 6,467,621 B1 | 10/2002 | Ishida | |
| 6,468,961 B1 | 10/2002 | Brodbeck et al. | |
| 6,469,132 B1 | 10/2002 | Eisenberg et al. | |
| 6,471,987 B1 | 10/2002 | McBride-Sakal et al. | |
| 6,477,428 B1 | 11/2002 | Skinner et al. | |
| RE37,950 E | 12/2002 | Dunn et al. | |
| 6,673,767 B1 | 1/2004 | Brodbeck et al. | |
| 6,742,522 B1 | 6/2004 | Baker et al. | |
| 6,747,121 B2 | 6/2004 | Gogolewski | |
| 6,845,352 B1 | 1/2005 | Wang | |
| 6,846,352 B2 | 1/2005 | Yatake | 106/31.58 |
| 6,846,795 B2 | 1/2005 | Lant et al. | |
| 6,849,426 B2 | 2/2005 | Chen et al. | |

(Continued)

FOREIGN PATENT DOCUMENTS

| | | |
|---|---|---|
| CA | 2705520 | 5/2009 |
| EP | 0306212 | 3/1989 |
| EP | 1375557 | 2/2004 |
| EP | 1 917 971 A1 | 5/2008 |
| EP | 2050474 | 4/2009 |
| EP | 2123312 | 5/2009 |
| EP | 2219620 | 8/2010 |
| EP | 2611868 | 7/2013 |
| JP | 08206191 | 8/1996 |
| JP | 11181077 | 7/1999 |

(Continued)

OTHER PUBLICATIONS

Sakkas, P., Annals of General Hospital Psychiatry, Published Dec. 23, 2003, pp. 1.*

(Continued)

*Primary Examiner* — Brian-Yong Kwon
*Assistant Examiner* — Lyndsey Beckhardt
(74) *Attorney, Agent, or Firm* — Pauly, DeVries Smith & Deffner, L.L.C.

(57) ABSTRACT

Disclosed are terpolymer compositions of lactide, glycolide, and caprolactone and methods of making such polymers with an initiator. Methods of using the terpolymers as a drug delivery platform are also disclosed.

8 Claims, 13 Drawing Sheets

(56) References Cited

U.S. PATENT DOCUMENTS

| | | | |
|---|---|---|---|
| 6,852,816 B2 | 2/2005 | Lewis et al. | |
| 6,923,985 B2 | 8/2005 | Peterson et al. | |
| 6,936,052 B2 | 8/2005 | Gellman et al. | |
| 6,939,569 B1 | 9/2005 | Green et al. | |
| 7,008,979 B2 | 3/2006 | Schottman et al. | |
| 7,022,343 B2 | 4/2006 | Philbrook et al. | |
| 7,053,209 B1 | 5/2006 | Gibson et al. | |
| 7,074,426 B2 | 7/2006 | Kochinke | |
| 7,122,205 B2 | 10/2006 | Peterson et al. | |
| 7,128,927 B1* | 10/2006 | Dunn | 424/423 |
| 7,153,520 B2 | 12/2006 | Seo et al. | |
| 7,299,905 B2 | 11/2007 | Yamaguchi et al. | |
| 7,368,126 B2 | 5/2008 | Chen et al. | |
| 7,798,954 B2 | 9/2010 | Birk et al. | |
| 8,025,635 B2 | 9/2011 | Eaton et al. | |
| 8,492,512 B2 | 7/2013 | Raiche et al. | |
| 8,920,921 B2 | 12/2014 | Bowman et al. | |
| 8,951,546 B2 | 2/2015 | Tice | |
| 2001/0000142 A1 | 4/2001 | Santos et al. | |
| 2002/0150622 A1 | 10/2002 | Philbrook et al. | |
| 2003/0026967 A1 | 2/2003 | Joseph et al. | |
| 2003/0068600 A1 | 4/2003 | Ellison | |
| 2003/0114637 A1* | 6/2003 | Gogolewski | 528/354 |
| 2003/0185872 A1 | 10/2003 | Kochinke | |
| 2003/0203991 A1 | 10/2003 | Schottman et al. | |
| 2004/0006199 A1 | 1/2004 | Newman, Jr. et al. | |
| 2004/0037885 A1* | 2/2004 | Seo et al. | 424/486 |
| 2004/0052859 A1 | 3/2004 | Wu et al. | |
| 2004/0116025 A1 | 6/2004 | Gogins et al. | |
| 2004/0146546 A1 | 7/2004 | Gravett et al. | |
| 2004/0224132 A1 | 11/2004 | Roe et al. | |
| 2005/0008671 A1 | 1/2005 | Van Antwerp | |
| 2005/0079202 A1* | 4/2005 | Chen et al. | 424/426 |
| 2005/0129732 A1 | 6/2005 | Rubsamen | |
| 2005/0267543 A1 | 12/2005 | Heruth et al. | |
| 2006/0039952 A1 | 2/2006 | Yaacobi | |
| 2006/0147491 A1 | 7/2006 | DeWitt et al. | |
| 2006/0212113 A1 | 9/2006 | Shaolian et al. | |
| 2007/0005094 A1 | 1/2007 | Eaton et al. | |
| 2007/0184084 A1 | 8/2007 | Chen et al. | 424/422 |
| 2007/0190154 A1 | 8/2007 | Zeigerson | |
| 2007/0202145 A1 | 8/2007 | Ghabrial et al. | |
| 2007/0207189 A1 | 9/2007 | Belcheva et al. | |
| 2007/0231365 A1 | 10/2007 | Wang et al. | |
| 2007/0265645 A1 | 11/2007 | Birk et al. | |
| 2008/0051868 A1 | 2/2008 | Cottone et al. | |
| 2008/0118541 A1 | 5/2008 | Pacetti | |
| 2008/0125728 A1 | 5/2008 | Bischoff et al. | |
| 2008/0208323 A1 | 8/2008 | El-kurdi et al. | |
| 2008/0260796 A1 | 10/2008 | Bischoff et al. | |
| 2009/0004243 A1 | 1/2009 | Pacetti et al. | |
| 2009/0124535 A1 | 5/2009 | Markland et al. | |
| 2009/0198197 A1 | 8/2009 | Bischoff et al. | |
| 2009/0306120 A1 | 12/2009 | Lim et al. | |
| 2010/0098744 A1 | 4/2010 | Ferris et al. | |
| 2010/0158969 A1 | 6/2010 | Tice | |
| 2010/0158970 A1 | 6/2010 | Tipton et al. | |
| 2010/0158978 A1 | 6/2010 | Markland | |
| 2010/0160891 A1 | 6/2010 | Tipton et al. | |
| 2010/0160892 A1 | 6/2010 | Tice | |
| 2010/0168807 A1 | 7/2010 | Burton et al. | |
| 2010/0198278 A1 | 8/2010 | Cobian et al. | |
| 2010/0203100 A1 | 8/2010 | Cobian et al. | |
| 2010/0247596 A1 | 9/2010 | Bischoff | |
| 2011/0098813 A1 | 4/2011 | Gibson | |
| 2011/0129422 A1 | 6/2011 | Markland et al. | |
| 2011/0159072 A1 | 6/2011 | Missling et al. | |
| 2012/0077028 A1 | 3/2012 | Bowman et al. | |
| 2012/0077887 A1 | 3/2012 | Bowman et al. | |
| 2012/0077954 A1 | 3/2012 | Raiche et al. | |
| 2012/0078155 A1 | 3/2012 | Bowman et al. | |

FOREIGN PATENT DOCUMENTS

| | | |
|---|---|---|
| JP | 11343228 | 12/1999 |
| JP | 2000159865 | 6/2000 |
| JP | 2000508931 | 7/2000 |
| JP | 2004514734 | 5/2004 |
| JP | 2012513473 | 6/2012 |
| JP | 2013543521 | 12/2013 |
| WO | 9738676 | 10/1997 |
| WO | 0245689 | 6/2002 |
| WO | 2006124021 | 11/2006 |
| WO | WO 2006124021 | 11/2006 |
| WO | 2009064442 | 5/2009 |
| WO | WO-2009-064442 | 5/2009 |
| WO | 2010075298 | 7/2010 |
| WO | WO-2010-075298 | 7/2010 |
| WO | 2012030819 | 3/2012 |
| WO | 2012030821 | 3/2012 |
| WO | 2012030822 | 3/2012 |
| WO | 2012030823 | 3/2012 |

OTHER PUBLICATIONS

Srisa-ard, Mangkorn et al., Polym Int 50:891-896 (2001).*

International Search Report & Written Opinion for PCT/US2008/012755 mailed Jan. 21, 2009.

Kulkarni et al. "Poly(lactic acid) for surgical implants," *Arch Surg.* 93(5):839-843 (1966).

Miller et al., Degradation rates of oral restorable implants (polylactates and polyglycolates): Rate modification with changes in PLA/PGA copolymer ratios, *J. Biomed. Mater. Res.* 11:711-719 (1977).

Sawhney et al., "Rapidly degraded terpolymers of d,l-lactide, glycolide and ε-caprolactone with increased hydrophilicity by copolymerization with polyethers," *J. Biomed. Mater. Res.* 24:1397-1411 (1990).

Stolnik et al., Polylactide-poly (ethylene glycol) micellar-like particles as potential drug carriers: Production, colloidal properties and biological performance, *J. Drug Targeting* 9:361-378 (2001).

International Search Report from PCT/US2009/069024 mailed Nov. 26, 2010.

Gollwitzer et al., "Antibacterial poly(D,L-lactic acid) coating of medical implants using a biodegradable drug delivery technology," Journal of Antimicrobial Chemotherapy, vol. 51:585-591, 2003.

Hong et al., "Generating Elastic, Biodegradable Polyurethane/ Poly(lactide-co-glycolide) Fibrous Sheets with Controlled Antibiotic Release via Two-Stream Electrospinning," Biomacromolecules, vol. 9:1200-1207, 2008.

Amendments before examination filed on Jul. 27, 2010 for EP Pat. App. No. 08850639.9, which claims priority to Intl. App. No. PCT/US08/012755, filed Nov. 12, 2008 (Inventor—Markland et al.; Applicant—Surmodics Pharmaceuticals, Inc.).

Intl. Report on Patentability issued on May 18, 2010 for Intl. App. No. PCT/US08/012755, filed Nov. 12, 2008 (Inventor—Markland et al.; Applicant—Surmodics Pharmaceuticals, Inc.).

Intl. Report on Patentability issued on Jul. 7, 2011 for Intl. App. No. PCT/US09/069024, filed Dec. 21, 2009 (Inventor—Tipton et al.; Applicant—Surmodics Pharmaceuticals, Inc.).

Intl. Search Report with Written Opinion issued on Nov. 26, 2010 for Intl. App. No. PCT/US09/069024, filed Dec. 21, 2009 (Inventor—Tipton et al.; Applicant—Surmodics Pharmaceuticals, Inc.).

Non-Final Rejection issued on Aug. 3, 2011 for U.S. Appl. No. 12/643,558, filed Dec. 21, 2009 (Inventor—T. Tice).

Response after Non-Final Rejection filed on Aug. 17, 2011 for U.S. Appl. No. 12/643,571, filed Dec. 21, 2009 (Inventor—T. Tice).

Non-Final Rejection issued on Jun. 8, 2011 for U.S. Appl. No. 12/643,571, filed Dec. 21, 2009 (Inventor—T. Tice).

Response to Restriction/Election Requirement filed on Mar. 29, 2011 for U.S. Appl. No. 12/643,571, filed Dec. 21, 2009 (Inventor—T. Tice).

Restriction/Election Requirement issued on Feb. 2, 2011 for U.S. Appl. No. 12/643,571, filed Dec. 21, 2009 (Inventor—T. Tice).

(56) References Cited

OTHER PUBLICATIONS

Beletsi, A et al., "Effect of Preparative Variables on the Properties of poly(dl-lactide-co-glycolide)—methoxypoly (ethyleneglycol) Copolymers Related to Their Application in Controlled Drug Delivery", International Journal of Pharmaceuticals, 182 (1999) pp. 187-197.

Bodansky, M. et al., "Utilization of Poly Glycerol Esters", Ed. Principles of Peptide Synthesis, Springer-Verlag, Inc, N.Y., 1993, (p. 1938-1942).

Final Office Action, for U.S. Appl. No. 12/644,097, mailed Feb. 28, 2013 (28 pages).

Final Office Action, for Japanese Patent Application No. 2010-534036, mailed Nov. 6, 2013 (4 pages) with English translation.

Final Office Action, for U.S. Appl. No. 12/644,097, mailed Apr. 9, 2014 (20 pages).

Final Office Action, for U.S. Appl. No. 13/221,389, mailed Sep. 10, 2013 (38 pages).

Final Office Action, from U.S. Appl. No. 12/643,558, mailed May 10, 2013, 15 pages.

Final Office Action, mailed Apr. 9, 2012 in co pending U.S. Appl. No. 12/644,097, "Bioactive Terpolymer Compositions and Methods of Making and Using Same," (16 pages).

Final Office Action, mailed Dec. 2, 2011 in co pending U.S. Appl. No. 12/643,558, "Flexible Implantable Composites and Implants Comprising Same," (19 Pages).

"Final Office Action", mailed May 18, 2012 in U.S. Appl. No. 12/643,546, "Elastic Implantable Composites and Implants Comprising Same," (11 pages).

"Final Office Action", mailed Oct. 28, 2011 in co pending U.S. Appl. No. 12/643,571, "Implantable Suction Cup Composites and Implants Comprising Same," (22 pages).

"Final Office Action", mailed Sep. 27, 2012 in U.S. Appl. No. 12/643,580, "Bioactive Spray Coating Compositions and Methods of Making and Uses Thereof," (8 pages).

Gollwitzer, et al., "Antibacterial poly(D,L-lactic acid) coating of medical implants using a biodegradable drug delivery technology", Journal of Antimicrobial Chemotherapy, 2003, pp. 585-591.

Grant "Synthetic Peptides: A User Guide", W.H. Freemean and Co., N. Y., 1992, (25 pgs).

Harlow, Ed, "Antibodies, a Laboratory Manual", Cold Spring Harbor Publications, N. Y., 1988, (4 pages).

Hong, et al., "Generating Elastic, Biodegradable Poolyurethane/Poly(lactide-co-glycolide) Fibrous Sheets with Controlled Antibiotic Release via Two-Stream Electrospinning", Biomacromolecules, 9, 2008, pp. 1200-1207.

"International Preliminary Report on Patentability", from International Application No. PCT/US2008/012755, mailed May 18, 2010, (5 pages).

"International Preliminary Report on Patentability", from PCT Application No. PCT/US2011/049730, mailed Mar. 14, 2013, 8 pages.

International Preliminary Report on Patentability, from PCT Application No. PCT/US2011/049731, mailed Mar. 14, 2013, 6 pages.

International Preliminary Report on Patentability, from PCT Application No. PCT/US2011/049735, mailed Mar. 14, 2013, 10 pages.

International Preliminary Report on Patentability, from PCT/US2011/049726, mailed Mar. 14, 2013, 8 pages.

"International Search Report and Written Opinion", from International Application No. PCT/US2008/012755, mailed Jan. 29, 2009, (6 pages).

"International Search Report and Written Opinion", from International Application No. PCT/US2009/069024, mailed Nov. 26, 2010, (16 pages).

"International Search Report and Written Opinion", from International Application No. PCT/US2011/049726, mailed Nov. 18, 2011, pp. 1-11.

"International Search Report and Written Opinion", from International Application No. PCT/US2011/049730, mailed Nov. 18, 2011, pp. 1-20.

"International Search Report and Written Opinion", from International Application No. PCT/US2011/049731, mailed Feb. 14, 2012, pp. 1-9.

"International Search Report and Written Opinion", from International Application No. PCT/US2011/049735, mailed Nov. 18, 2011, pp. 1-15.

Kastin, Abba J., "Handbook of Biologically Active Peptides", Academic Press, 2006, (6 pages).

Kobayashi, et al., "Bioconjugate Chem", vol. 12, pp. 100-107, (2001).

Kobayashi, et al., "Mag Res in Medicine", vol. 46, pp. 579-85, (2001).

Kulkarni, et al., "Poly(lactic acid) for Surgical Implants", Technical Rep. 6608, Walter Reed Army Medical Center, Washington, D.C., 1966.

Letsinger, et al., "Proceedings of the National Academy of Sciences", vol. 86, pp. 6553-6556, 1989.

Miller, et al., "Degradation Rates of Oral Resorbable Implants (polylactates and polyglycolates): Rate Modification with Changes in PLA/PGA Copolymer Ratios", J. Biomed. Matr. Res. 11, 1977, pp. 711-719, (12 pages).

Mundargi, Raghavendra C. et al., "Development and Evaluation of Novel Biodegradable Microspheres Based on poly(D,L-Lactide-co-glycolide) and poly(e-caprolactone) for Controlled Delivery of Doxycyline in the Treatment of Human Periodontal Pocket: In Vitro and In Vivo Studies", Journal of Controlled Release, vol. 119, 2007, pp. 59-68.

Nagy, et al., "Immunomodulation by tamoxifen and pergolide", Immunopharmacology, 12(2), Oct. 1986, pp. 1-2 (abstract only, pp. 1,2).

Nielson, Peter E. et al., "Bioconjug. Chem.", vol. 5, pp. 3-7, 1994.

"Non-Final Office Action", mailed Mar. 16, 2012 in co-pending U.S. Appl. No. 12/643,580, "Bioactive Spray Coating Compositions and Methods of Making and Uses Thereof," (31 Pages).

"Non-Final Office Action", mailed Oct. 11, 2011 in co-pending U.S. Appl. No. 12/644,097, "Bioactive Terpolymer Compositions and Methods of Making and Using Same" (48 pages).

"Non-Final Office Action", for U.S. Appl. No. 12/643,580, mailed May 20, 2014 (10 pages).

"Non-Final Office Action", for U.S. Appl. No. 13/221,464, mailed May 9, 2014 (33 pages).

"Non-Final Office Action", for U.S. Appl. No. 12/644,097, mailed Jul. 19, 2013 (37 pages).

"Non-Final Office Action", for U.S. Appl. No. 12/643,558, mailed Apr. 1, 2014 (26 pages).

"Non-Final Office Action", for U.S. Appl. No. 13/221,415, mailed Feb. 6, 2014 (16 pages).

"Non-Final Office Action", from U.S. Appl. No. 12/643,546, mailed Jun. 19, 2013, 12 pages.

"Non-Final Office Action", from U.S. Appl. No. 13/221,389, mailed Apr. 9, 2013, 17 pages.

"Non-Final Office Action", mailed Jan. 7, 2013 in co-pending U.S. Appl. No. 12/643,558, "Flexible Implantable Composites and Implants Comprising Same," (15 pages)., 15.

"Non-Final Office Action", mailed Dec. 15, 2011 in co-pending U.S. Appl. No. 12/643,546, 32 pages.

"Non-Final Office Action", mailed Jul. 5, 2012 in co-pending U.S. Appl. No. 13/221,429, "Process for Reducing Moisture in a Biodegradable Implant Device" (6 pages).

"Non-Final Office Action", mailed Jun. 8, 2011, in co-pending U.S. Appl. No. 12/643,571, (11 pages).

"Non-Final Office Action", mailed Sep. 20, 2012 in U.S. Appl. No. 12/644,097, "Bioactive Terpolymer Compositions and Methods of Making and Using Same," (38 pages).

"Notice of Allowance", for U.S. Appl. No. 12/643,546, mailed Feb. 21, 2014 (8 pages).

"Notice of Allowance", for U.S. Appl. No. 12/643,546, mailed Jun. 11, 2014 (14 pages).

"Notice of Allowance", from U.S. Appl. No. 13/221,429, mailed Mar. 22, 2013, 20 pgs.

Notice of Allowance, mailed Oct. 23, 2012 in U.S. Appl. No. 13/221,429, "Process for Reducing Moisture in a Biodegradable Implant Device," (5 pages).

(56) References Cited

OTHER PUBLICATIONS

Office Action, from JP Application No. 2010-534036, mailed Jun. 11, 2013, 7 pages.
Remington,, "The Science and Practice of Pharmacy", 21st Ed., Lippincott Williams & Wilkins, Philadelphia, PA, 2005, (14 pages).
Response to Final Office Action, for U.S. Appl. No. 12/643,558, mailed May 10, 2013 and filed with the USPTO Aug. 2, 2013 (7 pages).
"Response to Final Office Action", for U.S. Appl. No. 13/221,389, mailed Sep. 10, 2013 and filed with USPTO Jan. 10, 2014 (9 pages).
"Response to Final Office Action", mailed Aug. 20, 2012 in co-pending U.S. Appl. No. 12/643,546 9 pages.
"Response to Final Office Action", mailed Dec. 27, 2012 in U.S. Appl. No. 12/643,580, "Bioactive Spray Coating Compositions and Methods of Making and Uses Thereof", 5 pages.
"Response to Final Office Action", mailed Feb. 28, 2013, in co-pending U.S. Appl. No. 12/644,097, filed with USPTO May 24, 2013, (12 pages).
"Response to Final Office Action", mailed Jan. 26, 2012 in co-pending U.S. Appl. No. 12/643,571 11 pages.
"Response to Final Office Action", mailed Jul. 9, 2012 in U.S. Appl. No. 12/644,097, "Bioactive Terpolymer Compositions and Methods of Making an Dusing Same", (10 pages).
"Response to Final Office Action", mailed Mar. 2, 2012 in co-pending U.S. Appl. No. 12/643,558 10 pages.
"Response to Non Final Office Action", mailed Jan. 3, 2012 in U.S. Appl. No. 12/644,097, "Bioactive Terpolymer Compositions and Methods of Making and Using Same", (8 pages).
"Response to Non Final Office Action", mailed Oct. 31, 2011 in U.S. Appl. No. 12/643,558, "Flexible Implantable Composites and Implants Comprising Same", (8 pages).
"Response to Non-Final Office Action", for U.S. Appl. No. 12/643,546, mailed Jun. 19, 2013 and filed with the USPTO Dec. 19, 2013 (7 pages).
"Response to Non-Final Office Action", for U.S. Appl. No. 12/644,097, mailed Jul. 19, 2013 and filed with the USPTO Dec. 19, 2013 (7 pages).
"Response to Non-Final Office Action", for U.S. Appl. No. 13/221,415, mailed Feb. 6, 2014 and filed with the USPTO May 6, 2014 (13 pages).
"Response to Non-Final Office Action", mailed Apr. 9, 2013, in co-pending U.S. Appl. No. 13/221,389, filed with USPTO Jul. 2, 2013 (9 pages).
"Response to Non-Final Office Action", mailed Jan. 7, 2013, in co-pending U.S. Appl. No. 12/643,558, filed with USPTO Apr. 8, 2013, (9 pages).
"Response to Non-Final Office Action", mailed Jun. 14, 2012 in co-pending U.S. Appl. No. 12/643,580 6 pages.
"Response to Non-Final Office Action", mailed Jun. 8, 2011, in co-pending U.S. Appl. No. 12/643,571, filed with USPTO Aug. 17, 2011, (10 pages).
"Response to Non-Final Office Action", mailed Mar. 14, 2012 in co-pending U.S. Appl. No. 12/643,546 8 pages.
"Response to Non-Final Office Action", mailed Oct. 2, 2012 in co-pending U.S. Appl. No. 13/221,429 5 pages.
"Response to Non-Final Office Action", mailed Sep. 20, 2012, in co-pending U.S. Appl. No. 12/644,097, filed with USPTO Jan. 18, 2013, (10 pages).
"Response to Restriction Requirement", mailed Feb. 6, 2012 in co-pending U.S. Appl. No. 12/643,580 5 pages.
"Restriction Requirement", for U.S. Appl. No. 13/022,720, mailed Apr. 30, 2014 (8 pages).
"Restriction Requirement", mailed Jan. 6, 2012 in co-pending U.S. Appl. No. 12/643,580, "Bioactive Spray Coating Compositions and Methods of Making and Uses Thereof," (6 pages).
Sakkas, P, "The Future: Towards Long Acting Atypical Anti-Psychosis", Annals of General Hospital Psychiatry, Oral Presentation, Dec. 23, 2003, 1 pg.
Sawhney,, "Rapidly degraded terpolymers of dl-lactide, glycolide, and [epsilon]—caprolactone with increased hydrophilicity by copolymerization with polyethers", Journal of Biomedical Materials Research, Wiley, New York, NY, US vol. 24, No. 10, Oct. 1, 1990, pp. 1397-1411.
Srisa-Ard, Mangkorn et al., "Synthesis and characterization of a random terpolymer of L-lactide, e-caprolactone and glycolide", Society of Chemical Industry, Polymer International, vol. 50, Issue 8 (Jul. 20, 2001) pp. 891-896.
Stolnik, et al., "Polylactide-Poly(ethylene glycol) micellar-like Particles as Potential Drug Carriers: Production, Colloidal Properties and Biological Performance", J. Drug Targeting, 2001 (18 pages).
Communication Pursuant to Rules 70(2) and 70a(2) EPC, for European Patent Application No. 08850639.9, mailed Dec. 5, 2014 (1 page).
"Extended European Search Report", for European Patent Application No. 08850639.9, mailed Nov. 19, 2014 (5 pages).
"Final Office Action", for U.S. Appl. No. 12/643,571, mailed on Jan. 5, 2015 (32 pages).
"Final Office Action", for U.S. Appl. No. 13/221,464 mailed on Dec. 4, 2014 (47 pages).
Lu, Chengfei et al., "Synthesis and Aggregation Behavior of four types of different Shaped PCL-PEG Block Copolymers", Polymer International, vol. 55, 2006, pp. 694-700.
"Non-Final Office Action", for U.S. Appl. No. 12/643,571, mailed Jul. 3, 2014 (19 pages).
"Non-Final Office Action", for U.S. Appl. No. 12/644,097, mailed Sep. 11, 2014 (26 pages).
"Non-Final Office Action", for U.S. Appl. No. 13/022,720, mailed Jul. 14, 2014 (35 pages).
"Non-Final Office Action", for U.S. Appl. No. 13/221,389, mailed Aug. 25, 2014 (22 pages).
"Notice of Allowance", for U.S. Appl. No. 12/643,546, mailed Oct. 1, 2014 (7 pages).
"Notice of Allowance", for U.S. Appl. No. 12/643,558, mailed Sep. 2, 2014 (14 pages).
"Notice of Allowance", for U.S. Appl. No. 13/221,415, mailed Aug. 1, 2014 (20 pages).
"Office Action", for Canadian Patent Application No. 2,705,520, mailed Jan. 20, 2015 (4 pages).
"Plastic", The Free Dictionary, 2014 (5 pages).
"Response to Final Office Action", Mailed Apr. 9, 2014 in co-pending U.S. Appl. No. 12/644,097, filed with the USPTO Jul. 9, 2014 (10 pages).
"Response to Non-Final Office Action", for U.S. Appl. No. 12/643,558, mailed Apr. 1, 2014 and filed with the USPTO Jul. 1, 2014 (7 pages).
"Response to Non-Final Office Action", for U.S. Appl. No. 12/643,571, mailed Jul. 3, 2014 and filed with the USPTO Oct. 3, 2014 (10 pages).
"Response to Non-Final Office Action", for U.S. Appl. No. 12/643,580, mailed May 20, 2014 and filed with the USPTO Nov. 20, 2014 (7 pages).
"Response to Non-Final Office Action", for U.S. Appl. No. 13/221,464, mailed May 9, 2014 and filed with the USPTO Sep. 9, 2014 (18 pages).
US 8,900,699, 12/2014, Bowman et al. (withdrawn)

* cited by examiner

VISCOUS TERPOLYMERS AS DRUG DELIVERY PLATFORM

CROSS REFERENCE TO RELATED APPLICATIONS

This application claims the benefit of priority to U.S. Provisional Application No. 60/987,648, filed Nov. 13, 2007, which is incorporated by reference herein in its entirety.

FIELD

The subject matter disclosed herein generally relates to the field of terpolymers and their uses in drug delivery.

BACKGROUND

Homopolymers of glycolide and lactide have been extensively studied and reported in literature. Such polymers have received wide acceptance in pharmacological applications due to their biodegradability and non-toxicity in vivo (see e.g., Kulkarni et al., "Poly(lactic acid) for surgical implants," *Technical Rep.* 6608, Walter Reed Army Medical Center, Washington, D.C., 1966). Copolymers of glycolide and lactide have also been used in medical applications due to an improvement in polymeric properties over the homopolymers. For example, copolymers of lactide and glycolide are less crystalline and the intermediate copolymeric compositions are more susceptible to hydrolytic attack than the homopolymers. Miller et al. reported a 10-fold increase in degradation on moving from homopolymers to copolymers of lactide and glycolide (Miller et al., "Degradation rates of oral resorbable implants (polylactates and polyglycolates): Rate modification with changes in PLA/PGA copolymer ratios," *J. Biomed. Mater. Res.,* 11:711-719, 1977).

It was noticed that hydrolysis rates of lactide-glycolide copolymers typically increase above the polymer glass transition temperature. Crystallinity and polymer chain orientation were shown to retard degradation. Irradiation, used for sterilization, was also shown to accelerate degradative processes. Thus, many have studied the effects of monomer ratios and different additives on lactide-glycolide copolymers in efforts to tailor specialty compositions with desirable properties.

It is often desired to prepare viscous formulations of polymers for drug delivery. In one example, ATRIX ATRIGEL™ is a poly(lactide-glycolide) polymer that can be prepared as a viscous liquid. However, it must be dissolved in relatively large quantities of organic solvents (like N-methylpyrrolidone) in order to form the viscous formulation. Typical polymer concentrations in the solvent are on the order of about 10% to 50%. Another high viscosity injectable is Durect's SABER™, which is a sucrose acetate isobutyrate that is a non-polymeric high-viscosity liquid that thins-out dramatically with the addition of small quantities of solvent (like ethanol). This makes it attractive in that only small quantities of solvent are needed to bring the viscosity of the material down to practical, injectable levels. However, the SABER™ material itself has few factors or variables that can be manipulated in order to adjust the attributes of the material as a platform-based technology.

Another drug-delivery platform involves polymeric micelles containing biodegradable, hydrophobic blocks. Polymeric micelles have been described where block copolymers comprising polycaprolactone (PCL) are the hydrophobic polymer core-forming components(s) and polyethylene glycol are the hydrophilic shell-forming components(s) (see e.g., U.S. Pat. No. 6,469,132). Such micelles can be particularly suited to carrying or solubilizing hydrophobic or lipophilic drugs having affinity towards (and that partition into) the hydrophobic cores of these particles.

Of the hydrophobic biodegradable polymers (such as polyesters based on lactide or caprolactone), PCL is often used because longer chain-length of the caprolactone produces a more hydrophobic polymer. However, PCL as a biodegradable, hydrophobic block suffers in that it is a crystalline to semi-crystalline polymer; PCL has a melting point of about 60° C. Crystallinity within the core of the polymeric micelle can be disadvantageous in that the crystalline regions are highly organized, tightly-structured areas that provide no room or space for carrying a drug load. Therefore, crystallinity will lower the drug-loading capacity of the resulting polymeric micelle. Another biodegradable polymer known to contain highly crystalline structures is poly(L-lactide).

What are needed are new biocompatible polymer compositions that can be viscous liquids or polymeric micelles and that have other unique properties suitable for certain pharmaceutical and medical applications. Compositions that are viscous liquids without the need for organic solvents or without large amounts of solvents are desired. It is also desired to have polymers with hydrophobic biodegradable core-forming blocks for preparing polymeric micelles and yet that do not also suffer from the disadvantages associated with the crystallinity of PCL. Also desired are compositions that can be easily modified to provide variability in terms of release, duration, and performance. The compositions and methods disclosed herein meet these and other needs.

SUMMARY

In accordance with the purposes of the disclosed materials, compounds, compositions, articles, and methods, as embodied and broadly described herein, the disclosed subject matter, in one aspect, relates to compositions and methods for preparing and using such compositions. In a further aspect, the disclosed subject matter relates to terpolymers of lactide, glycolide, and caprolactone. Methods of making and using such terpolymers are also disclosed. In yet a further aspect, the disclosed subject matter relates to viscous polymeric liquids and polymeric micelles comprised of biodegradable terpolymers of lactide, glycolide, caprolactone initiated with different hydroxyl-containing initiators, which provide (or impart) different characteristics (such as viscosity, hydrophilicity, degradation rate) to the final viscous polymer.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
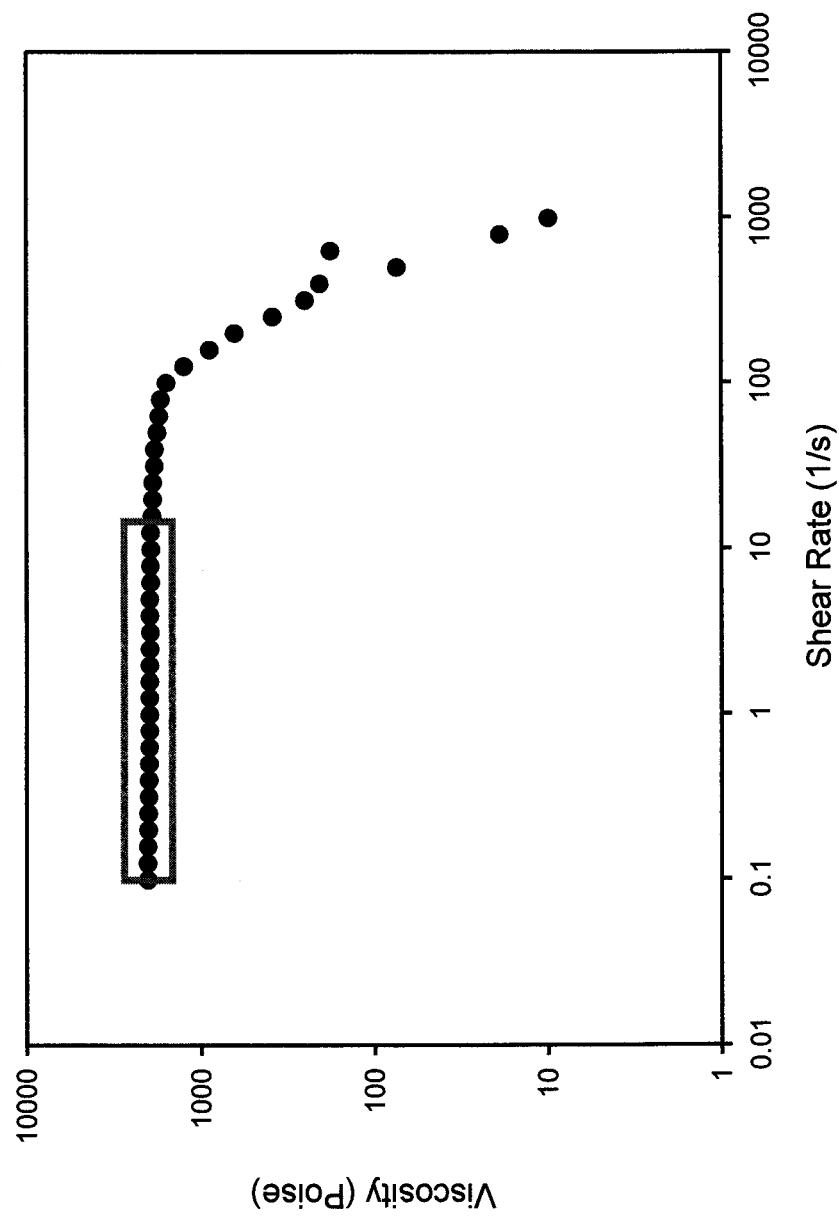
FIG. 1 is an example graph of stepped-shear viscosity (poise) versus shear rate ($sec^{-1}$). The highlighted data points show the region where viscosity is independent of shear rate from which the reported viscosity value is estimated.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General and Chemical Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a compound" includes mixtures of two or more such compounds, reference to "an agent" includes mixtures of two or more such agents, reference to "the composition" includes mixtures of two or more such compositions, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. The term "about" means within 5% of the stated value. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular component in a composition denotes the weight relationship between the component and any other components in the composition for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, a "mole percent" or "mole %" of a component, unless specifically stated to the contrary, refers to the ratio of the number of moles of the component to the total number of moles of the composition in which the component is included, expressed as a percentage.

"Contacting" means an instance of exposure by close physical contact of at least one substance to another substance.

"Admixture," "mixture," or "blend" is generally used herein to refer to a physical combination of two or more different components. In the case of polymers, an admixture, mixture, or blend of polymers is a physical blend or combination of two or more different polymers. Admixtures can, though need not, result in a reaction between the admixed components, resulting in a composition where little or none of the original components are present.

"Sufficient amount" and "sufficient time" mean an amount and time needed to achieve the desired result or results, e.g., dissolve a portion of the polymer.

"Biocompatible" as used herein refers to a material that is generally non-toxic to the recipient and does not possess any significant adverse effects to the subject and, further, that any metabolites or degradation products of the material are non-toxic to the subject.

"Biodegradable" refers to a material that will degrade or erode under physiologic conditions to smaller units or chemical species and are capable of being metabolized, eliminated, or excreted by the subject.

The general term "polymer" includes homopolymer, copolymer, terpolymer, etc. unless the context clearly dictates otherwise.

D,L-PLG is poly(D,L-lactide-co-glycolide) prepared from the indicated mole ratios of D,L-lactide and glycolide, respectively. In contrast, L-PLG is poly(L-lactide-co-glycolide) prepared from the indicated mole ratios of L-lactide and glycolide, respectively. D,L-PL is poly(D,L-lactide). L-PL is poly(l-lactide). The term lactide can refer to either D,L-lactide or to L-lactide or to D-lactide when used to refer to either the monomer alone or to polymers and copolymers containing lactide. As such, poly(lactide) (PL) can refer generally to either poly(D,L-lactide) or poly(L-lactide) or poly(D-lactide). Similarly, poly(lactide-co-glycolide) (PLG) can refer to poly(D,L-lactide-co-glycolide) or poly(L-lactide-co-glycolide) or poly(D-lactide-co-glycolide). PCL is polycaprolactone. The abbreviations L, G, CL are used herein to refer to lactide, glycolide, and caprolactone, respectively.

DLGCL is a terpolymer prepared from the indicated mole ratios of: D,L-lactide:glycolide:caprolactone, respectively. The terpolymer can be random or block. LGCL is a terpolymer prepared from the indicated mole ratios of L-lactide:glycolide:caprolactone, respectively. The terpolymer can be random or block.

"Molecular weight" as used herein, unless otherwise specified, refers to the relative average chain length of the bulk polymer. In practice, molecular weight can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Controlled release" as used herein means the use of a material to regulate the release of another substance.

"Bioactive agent" is used herein to include a compound of interest contained in the disclosed terpolymer compositions, such as therapeutic or biologically active compounds. It includes without limitation physiologically or pharmacologically active substances that act locally or systemically in the body. A biologically active agent is a substance used for, for example, the treatment, prevention, diagnosis, cure, or mitigation of disease or illness, a substance which affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, drugs, small-molecule drugs, vaccines, adjuvants, peptides, proteins, nucleic acids, nucleotides, and oligonucleotides. "Bioactive agent" includes a single such agent and is also intended to include a plurality of bioactive agents including, for example, combinations of two or more bioactive agents.

"Excipient" is used herein to include any other compound that can be contained in the disclosed terpolymer compositions that is not a therapeutically or biologically active compound. As such, an excipient should be pharmaceutically or biologically acceptable or relevant, for example, an excipient should generally be non-toxic to the subject. "Excipient" includes a single such compound and is also intended to include a plurality of excipients.

"Agent" is used herein to refer generally to compounds that are contained in or on a terpolymer composition. Agent can include a bioactive agent or an excipient. "Agent" includes a single such compound and is also intended to include a plurality of such compounds.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen and oxygen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. Also, as used herein "substitution" or "substituted with" is meant to encompass configurations where one substituent is fused to another substituent. For example, an aryl group substituted with an aryl group (or vice versa) can mean that one aryl group is bonded to the second aryl group via a single sigma bond and also that the two aryl groups are fused, e.g., two carbons of one alkyl group are shared with two carbons of the other aryl group.

"$A^1$," "$A^2$," "$A^3$," and "$A^4$" are used herein as generic symbols to represent various specific substituents. These symbols can be any substituent, not limited to those disclosed herein, and when they are defined to be certain substituents in one sentence it does not mean that, in another sentence, they cannot be defined as some other substituents.

The term "alkyl" as used herein is a branched or unbranched saturated hydrocarbon group of 1 to 40 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, octadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitro, nitrile, or thiol, as described below. A "lower alkyl" is an alkyl group with up to six carbon atoms, e.g., methyl, ethyl, propyl, butyl, pentyl, and hexyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "alkyl halide" specifically refers to an alkyl group that is substituted with one or more halides, e.g., fluorine, chlorine, bromine, or iodine. When "alkyl" is used in one sentence and a specific term such as "alkyl halide" is used in another, it is not meant to imply that the term "alkyl" does not also refer to specific terms such as "alkyl halide" and the like.

This practice is also used for other groups described herein. That is, while a term such as "heteroaryl" refers to both unsubstituted and substituted heteroaryl moieties, the substituted moieties can, in addition, be specifically identified herein; for example, a particular substituted heteroaryl can be referred to as, e.g., an "alkyl heteroaryl." Similarly, a substituted alkenyl can be, e.g., an "alkenyl halide," and the like. Again, the practice of using a general term, such as "heteroaryl," and a specific term, such as "alkyl heteroaryl," is not meant to imply that the general term does not also include the specific term.

The term "alkoxy" as used herein is an alkyl or cycloalkyl group bonded through an ether linkage; that is, an "alkoxy" group can be defined as —$OA^1$ where $A^1$ is alkyl or cycloalkyl as defined above. A "lower alkoxy" is an alkoxy group with up to six carbon atoms, e.g., methoxy, ethoxy, propoxy, butoxy, pentoxy, and hexoxy.

The term "alkenyl" as used herein is a hydrocarbon group of from 2 to 40 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitro, nitrile, or thiol.

The term "alkynyl" as used herein is a hydrocarbon group of 2 to 40 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitro, nitrile, or thiol.

The term "aryl" as used herein is a group that contains any carbon-based aromatic group including, but not limited to, benzene, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, azide, nitro, nitrile, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, cyclooctyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, azide, nitrile, silyl, or thiol.

The term "cycloalkenyl" as used herein is a non-aromatic carbon-based ring composed of at least three carbon atoms and contains at least one double bound, e.g., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, azide, nitrile, or thiol.

The term "cyclic group" is used herein to refer to either aryl groups (e.g., heteraryl, biaryl), non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula:

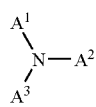

where $A^1$, $A^2$, and $A^3$ can each be, independent of one another, hydrogen, an alkyl, halogenated alkyl, alkenyl, alkynyl, aryl, heteroaryl, cycloalkyl, cycloalkenyl, heterocycloalkyl, or heterocycloalkenyl group described above. Also, any of the $A^1$, $A^2$, and $A^3$ substituents can be absent and any of the remaining substituents can be a multivalent group, i.e., form more than one bond with N.

The term "carboxylic acid" as used herein is represented by the formula —C(O)OH. The term "carboxylate" is a carboxylic acid that has been deprotonated, i.e., —C(O)O⁻. Protonation and deprotonation can be achieved by changes in pH. The terms "carboxylic acid" and "carboxylate" are understood to be interchangeable.

The term "ester" as used herein is represented by the formula —OC(O)$A^1$ or —C(O)O$A^1$, where $A^1$ can be a substituted or unsubstituted alkyl, cycloalkyl, alkenyl, cycloalkenyl, alkynyl, cycloalkynyl, aryl, or heteroaryl group as described herein.

The term "ether" as used herein is represented by the formula $A^1$O$A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein.

The term "halide" as used herein refers to the halogens fluorine, chlorine, bromine, and iodine.

The term "hydroxyl" as used herein is represented by the formula —OH.

The term "ketone" as used herein is represented by the formula $A^1$C(O)$A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$^2A^1$, or —OS(O)$_2$O$A^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or a substituted or unsubstituted alkyl, cycloalkyl, alkenyl, cycloalkenyl, alkynyl, cycloalkynyl, aryl, or heteroaryl group as described herein.

The term "sulfone" as used herein is represented by the formula $A^1$S(O)$_2A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula $A^1$S(O)$A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "sulfonamide" as used herein is represented by the formula —S(O)$_2$N$A^1$-, where $A^1$ can be hydrogen, a substituted or unsubstituted alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," and "$R^n$," where n is some integer, as used herein can, independently, possess two or more of the groups listed above. For example, if R is a straight chain alkyl group, one of the hydrogen atoms of the alkyl group can optionally be substituted with a hydroxyl group (OH), an alkoxy group, halide, etc. Depending upon the groups that are selected, a first group can be incorporated within second group or, alternatively, the first group can be pendant (i.e., attached) or fused to the second group.

The terms "ortho," "meta," and "para" refer to 1,2-, 1,3-, and 1,4-disubstituted benzenes, respectively.

As used herein, the term "alcohol" refers to compounds having at least one hydroxyl group (—OH). The term "polyol" is used to specifically refer to alcohols having two (which can specifically be referred to as a "diol") or more hydroxyl groups. Unless stated to the contrary the term "alcohol" is used herein to also refer to diols, triols, polyols and polymeric alcohols and polymeric polyols. Non-limiting examples of alcohols include methanol, ethanol, propanol, butanol, hexanol, octanol, decanol, dodecanol, oleyl alcohol, myristyl alcohol, cetyl alcohol, stearyl alcohol; short-chain alcohols (for example, $C_1$ to $C_6$ alcohols), medium-chain alcohols (for example, $C_7$ to $C_{12}$), long-chain alcohols (for example, $C_{13}$ to $C_{24}$ alcohols), and so on; saturated alcohols, unsaturated alcohols; benzyl alcohol, ethylene glycol, 1,3-propylene glycol, 1,2-propylene glycol, glycerol, and polymeric alcohols like modified polyvinyl alcohol, hydroxyl-containing PVP, and polyalkyleneoxy homo and copolymers, which can be alkoxy capped, for example, PEG, MPEG 600 and the like. Other examples of alcohols are disclosed elsewhere herein.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

It is understood that polymers are referenced herein by referring to the particular monomers that are used to make up the polymer. The monomers are, of course, not actually present in the polymer, except perhaps for some residual amount left over from the polymerization reaction. So, for example, polycaprolactone does not actually contain caprolactone (again except perhaps for some residual unreacted monomer); it contains repeating units from the ring-opened polymerized monomer caprolactone. This naming convention is common in the art.

Reference will now be made in detail to specific aspects of the disclosed materials, compounds, compositions, components, devices, articles, and methods, examples of which are illustrated in the following description and examples, and in the figures and their previous and following description.

Materials and Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components A, B, and C are disclosed as well as a class of components D, E, and F and an example of a combination composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Disclosed herein, in certain aspects, are terpolymers prepared using (hydroxyl-containing) alcoholic initiators. The choice and selection of the alcoholic initiator allows one methods by which the attributes of the final polymer can be changed or manipulated. For example, the final viscosity of the resulting terpolymer can be affected by selection of a lipid-like or long-chain alcoholic initiators or a low-viscosity alcoholic initiator. For example, a terpolymer as disclosed herein prepared using the lipid-like initiator 1-dodecanol or oleyl alcohol can have a lower viscosity than a similar terpolymer prepared from a small-molecular initiator (such as ethyl glycolate). Also, the relative lipophilicity of the resulting polymer can be affected by selection of a medium or long-chain (lipid-like) alcoholic initiator. The relative hydrophilicity of the resulting polymer can be affected by selection of a hydrophilic or a water-soluble alcoholic initiator (such as, for example, methoxy PEG-400). Hydrophobic initiators can be employed to slow down the relative degradation rate of a polymer while, conversely, a more hydrophilic initiator can result in a relatively faster degradation rate. The viscosity or rheological behavior of the resulting polymer can be affected by selection of a polymeric alcoholic initiator or by selection of an initiator containing two or more hydroxyl groups. Polyols can be used to prepare branched terpolymers having unusual rheological properties such as shear-thinning behavior or viscosities that are highly dependent on chain-length. Further, changes to the monomer composition allow additional routes by which the characteristics of the final polymer can be adjusted. For example, manipulations to the copolymer composition (such as increasing the relative caprolactone content, for example) can be utilized to lower the glass transition temperature, lower viscosity, alter hydrophobicity, and to affect manipulate overall degradation rates.

Terpolymers

Disclosed herein are compositions that comprise biodegradable and biocompatible terpolymers of lactide, glycolide, and ε-caprolactone initiated with a hydroxyl-containing initiator. A terpolymer is a polymer comprised of three distinct monomer repeat units. Terpolymers possessing a particular composition range of lactide (L), glycolide (G), and ε-caprolactone (CL) are reported in the literature to be "syrupy" in physical appearance (see Hubbell and Sawhney, "Rapidly degraded terpolymers of d,l-lactide, glycolide and ε-caprolactone with increased hydrophilicity by copolymerization with polyethers," *J. Biomed. Mater. Res.*, 24:1397-1411, 1990) which is incorporated herein by this reference in its entirety and especially for its teachings of terpolymers and methods of making and using them. Because of the significantly different properties glycolide, lactide, and ε-caprolactone have, one can have significant control over the polymer morphology and properties by varying the amounts of these monomers in the terpolymer. One can also have control over the viscosity, hydrophilicity, degradation rate, and/or flow properties of the disclosed terpolymers by varying the molecular weight and initiator.

The disclosed terpolymer compositions are, in certain examples, a viscous, liquid-polymeric drug delivery platform capable of being administered by injection. In another aspect, they can be used to form polymeric micelles capable of solubilizing hydrophobic and lipophilic drugs for oral, topical, or injection administration. Also disclosed are methods of using the disclosed terpolymer compositions as a polymeric micellar or viscous drug-delivery platform for controlled drug delivery. The formulations comprised of the disclosed terpolymers can contain a secondary component such as a bioactive agent in the terpolymer compositions itself; or, alternatively, the formulation can comprise of the terpolymer that is plasticized with small levels of biocompatible solvents (ethanol, among others, as an example).

In the disclosed terpolymers, lactide can be present in an amount of from about 10 to about 60 mole percent. For example, the lactide can be present in an amount of from about 10 to about 30 mole percent, from about 20 to about 40 mole percent, from about 30 to about 50 mole percent, from about 40 to about 60 mole percent, from about 50 to about 60 mole percent, from about 10 to about 20 mole percent, from about 20 to about 30 mole percent, from about 25 to about 45 mole percent, from about 45 to about 60 mole percent, from about 10 to about 25 mole percent, from about 12 to about 18, or from about 13 to about 16 mole percent. In other examples, lactide can be present in about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mole percent, where any of the stated values can form an upper or lower endpoint of a range. In a specific example, the disclosed terpolymers comprise about 15 mole % of lactide.

In the disclosed terpolymers, glycolide can be present in an amount of from about 10 to about 40 mole percent. For example, the glycolide can be present in an amount of from about 10 to about 20, from about 20 to about 30, from about 30 to about 40, from about 15 to about 25, from about 25 to about 35, from about 22 to about 28, or from about 24 to about 26 mole percent. In other examples, glycolide can be present in about 10, 11, 12, 13, 14, 15, 16, 17, 18, 19, 20, 21, 22, 23, 24, 25, 26, 27, 28, 29, or 30 mole percent, where any of the stated values can form an upper or lower endpoint of a range. In a specific example, the disclosed terpolymers comprise about 25 mole % of glycolide.

In the disclosed terpolymers, ε-caprolactone can be present in an amount of from about 20 to about 70 mole percent. For example, the ε-caprolactone can be present in an amount of from about 20 to about 50 mole percent, from about 30 to about 60 mole percent, from about 40 to about 70 mole percent, from about 20 to about 40 mole percent, from about 20 to about 30 mole percent, from about 30 to about 50 mole percent, from about 40 to about 60 mole percent, from about 50 to about 70 mole percent, from about 40 to about 50, from about 50 to about 60, from about 60 to about 70, from about 40 to about 55, from about 45 to about 60, from about 45 to about 65, from about 55 to about 65, or from about 58 to about 63 mole percent. In other examples, ε-caprolactone can be present in about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mole percent, where any of the stated values can form an upper or lower endpoint of a range. In a specific example, the disclosed terpolymers comprise about 60 mole % of ε-caprolactone.

The disclosed terpolymer can have viscosities ranging from highly viscous to low viscosity. They can be a sticky wax or paste to a flowable or injectable liquid. For example, the disclosed terpolymers have an inherent viscosity measured at 0.5% (wt/vol) terpolymer in chloroform at 30° C. of from about 0.02 to 0.25. In other examples, the inherent viscosity can be from about 0.02 to about 0.10, from about 0.05 to about 0.15, from about 0.10 to about 0.25, from about 0.12 to about 0.18, from about 0.14 to about 0.16, from about 0.11 to about 0.19, from about 0.13 to about 0.17, from about 0.11 to about 0.15, or from about 0.12 to about 0.17. In specific examples, the inherent viscosity measured at 0.5% (wt/vol) terpolymer in chloroform at 30° C. is about 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25, where any of the stated values can form an upper or lower endpoint of a range.

The Mw of the disclosed terpolymers can be less than about 25,000, for example, from about 650 to about 25,000 Daltons. In other examples, the Mw can be from about 650 to about 8,000, from about 1,000 to about 6,000, from about 1,000 to about 4,000, from about 1,500 to about 2,500, from about 7,000 to about 14,000, from about 8,000 to about 13,000, from about 9,000 to about 12,000, from about 10,000 to about 11,000, from about 6,000 to about 10,000, or from about 7,000 to about 11,000 Daltons. In specific examples, the Mw can be about 650, 750, 850, 950, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, or 25,000 Daltons, where any of the stated values can form an upper or lower endpoint of a range.

The Mn of the disclosed terpolymers is less than 15,000 Daltons. More typically the Mn is from about 500 to about 8,000 Daltons. For example, the Mn can be from about 500 to about 2,000, from about 500 to about 4,000, from about 500 to about 6,000, from about 500 to about 7,000, from about 2,000 to about 12,000, from about 2,000 to about 10,000, from about 2,000 to about 8,000, from about 2,000 to about 6,000, from about 3,000 to about 6,000, from about 4,000 to about 5,000, from about 2,000 to about 5,000, from about 4,000 to about 8,000, or from about 5,000 to about 6,000 Daltons. In specific examples, the Mn can be from about 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, or 15,000 Daltons, where any of the stated values can form an upper or lower endpoint of a range.

The polydispersity of the disclosed terpolymers can be from about 1.0 to about 3.0. For example, polydispersity can be from about 1.0 to about 2.5, from about 1.5 to about 3.0, from about 1.0 to about 2.0, from about 1.5 to about 2.5. In specific examples, the polydispersity can be 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0, where any of the stated values can form an upper or lower endpoint of a range.

The disclosed terpolymers can have a glass transition temperature (Tg) of less than about 20° C. For example, the Tg can be less than about 15, less than about 10, less than about 5, less than about 0, less than about minus 5, less than about minus 10, less than about minus 15, less than about minus 20, less than about minus 25, less than about minus 30, less than about minus 35, or less than about minus 40° C.

The disclosed terpolymers can have a residual amount of any one of the monomers (i.e., either lactide, glycolide, or caprolactone) of about 3.0 or less weight %, based on the total weight of the terpolymer. For example, the amount of any one of the residual monomers in the disclosed terpolymers can be less than about 2.5, less than about 2.0, less than about 1.5, less than about 1.0, less than about 1.0, less than about 0.5, or less than about 0.2 weight percent, where any of the stated values can form an upper or lower endpoint of a range.

While not wishing to be bound by theory, the free volume of an amorphous polymer increases once the temperature rises above the Tg. Thermal energy serves to create additional empty space between polymer chains allowing for increased local segmental motion. Above the Tg, an amorphous polymer behaves more like a rubbery liquid than a glassy solid. For a given polymer type, the Tg increases with number average molecular weight. Above some high degree of polymerization, Tg's tend to level off. The reason for this being that for low molecular weight polymers, the relative abundance of polymer chain-ends, which do not pack efficiently, contribute to additional free volume in the system. For this reason the present disclosure describes terpolymers with a weight average molecular weight of less than about 50,000 g/mol, or more particularly less than about 25,000 g/mol. Further, the disclosed terpolymers are expected to be amorphous over the entire expected working temperature range.

The disclosed terpolymers are synthesized using different hydroxyl-containing initiators which provide different characteristics to the polymer product. As such, disclosed herein are methods of forming a terpolymer by the addition of an initiator, in the presence of an appropriate catalyst, to a fixed amount of monomer. The initiator will be incorporated in the polymer and can be thought of as an end-group-producing substance. The Tg and viscosity can be further reduced by using initiating fragments that serve to frustrate polymer packing and thus increase free volume.

Further, in the disclosed terpolymers, the hydrophobic biodegradable blocks(s) used to form the polymeric micelle core comprises amorphous forming, random sequences of lactide, glycolide and caprolactone. The hydrophilic shell is comprised of polar, hydrophilic initiator fragments, such as polyethylene glycol and methoxy end-caped polyethylene glycol or other suitably polar segments such as a hydroxy-containing polyvinyl pyrrolidone (PVP). In addition to initiator fragments, the hydrophilic block can be coupled to the hydrophobic core via standard coupling chemistries well know to the synthetic chemist.

Initiators

The initiator is an alcohol capable of generating a hydroxyl group through reaction with the monomer. The added alcoholic initiator is the predominant initiating species as opposed to any residual water that may be present from batch to batch as well as for a given batch depending upon factors such as its exposure to atmospheric moisture, i.e., length of storage. Thus, in certain aspects, the initiator is not water. Having a water initiator will result in a terpolymer molecule with a free acid group. Thus, the disclosed terpolymers are substantially free of free acids. By "substantially free" is meant that terpolymer with a free acid is present in the final terpolymer composition at less than about 5, 4, 3, 2, 1, 0.5, 0.25, or 0.1 mole %.

Initiators can be a primary alcohol (R—CH$_2$—OH), a secondary alcohol (RR'CH—OH), mixtures of more than one different primary alcohol, mixtures of more than one different secondary alcohol, or mixtures of primary and secondary alcohols, where R and R' can be a saturated or unsaturated, linear or branched, alkyl chain. R and R' can each possess heteroatoms such as oxygen or nitrogen. R and R' can each be a substituted or unsubstituted phenyl. After polymerization, the initiators become the end group(s) of the terpolymer and, as such, are covalently part of the terpolymer.

Suitable initiators are non-crystalline at and above room temperature. For example, a suitable initiator is viscous, waxy, semi-solid and/or liquid at and above room temperature. The initiators should also have a Tg (glass transition temperature) at and below room temperature. Further, suitable initiators are non-toxic and biocompatible. They should also be compatible (i.e., do not degrade) and are soluble with the disclosed terpolymers. While not wishing to be bound by theory, the initiators act to soften or plasticize the disclosed terpolymers.

Some specific examples of suitable initiators include, but are not limited to, short chain alcohols with from one to five carbon atoms (e.g., methanol, ethanol, n-propanol, isopropanol, 1-butanol, sec-butanol, isobutanol, tertbutanol, pentanol, and the like). Other suitable initiators include, but are not limited to, saturated and unsaturated long chain alcohols with from six to twenty two carbon atoms (e.g., 1-hexanol, 2-ethyl hexanol, 1-heptanol, 1-octanol (capryl alcohol), 1-nonanol, 1-decanol (capric alcohol), 1-undecanol, 1-dodecanol (lauryl alcohol), 1-tridecanol, 1-tetradecanol (myristyl alcohol), 1-pentadecanol, 1-hexadecanol (cetyl alcohol), 1-heptadecanol, 1-octadecanol (stearyl alcohol), isostearyl alcohol, oleyl alcohol, palmitoleyl alcohol, petroselenyl alcohol, vaccenyl alcohol, gyptol, linoleyl alcohol, linolenyl alcohol, ricinoleyl alcohol, and the like).

Still further examples of initiators include, but are not limited to, ethylene diol, diethylene diol, triethylene diol, neopentyl diol, 1,3-propane diol, glycerol, 1,4-butanediol, 1,2-butane diol, 1,3-butane diol, 1,5-pentane diol, 1,2-pentane diol, 1,3-pentane diol, pentaerythritol, 1,6-hexanediol, 1,3-hexanediol, 1,4-cyclohexanedimethanol, 1,10-decanediol, 2,2,4,4,-tetramethyl-1,3-cyclobutanediol, 3-methyl-2,4-pentanediol, 2-methyl-1,4-pentanediol, 2,2,4-trimethyl-1,3-pentanediol, 2-ethyl-1-1,3-hexanediol, 2,2-diethyl-1,3-propanediol, and mixtures thereof. Still further examples include, but are not limited to, (2R,3R)-butane-1,2,3,4-tetraol, (2S,3R)-butane-1,2,3,4-tetraol, (2R,3S)-butane-1,2,3,4-tetraol, (2S,3S)-butane-1,2,3,4-tetraol, (2R,3R, 4R)-pentane-1,2,3,4,5-pentaol, (2S,3R,4R)-pentane-1,2,3,4, 5-pentaol, (2R,3 S,4R)-pentane-1,2,3,4,5-pentaol, (2R,3R, 4S)-pentane-1,2,3,4,5-pentaol, (2S,3 S,4R)-pentane-1,2,3,4, 5-pentaol, (2S,3R,4S)-pentane-1,2,3,4,5-pentaol, (2R,3 S,4S)-pentane-1,2,3,4,5-pentaol, and (2S,3 S,4S)-pentane-1, 2,3,4,5-pentaol.

Another class of suitable initiators are mono-hydroxy poly (ethylene glycol), di-hydroxy poly(ethylene glycol), poly (ethlylenei glycol) derivatives and multi-functionalized (multi-hydroxyl) poly(ethylene glycol), and mixtures thereof.

Some additional examples of initiators are monofunctional alcohols $C_1$-$C_{24}$, difunctional alcohols, trifunctional alcohols, tetrafunctional alcohols, multi-functional alcohols, primary, secondary, and tertiary alcohols, saturated or unsaturated alcohols, hydroxy-containing carboxylic acids, hydroxy-containing fatty acids (including saturated or unsaturated hydroxy-containing fatty acids) (such as riconoleic acid), bile salts including cholic acid, chenodeoxycholic acid, glycocholic acid, taurocholic acid, deoxycholic acid and combinations thereof, hydroxy-containing amino acids, hydroxy-containing peptides, sugar alcohols, monosaccharides, disaccharides, sugar acids, glycol ethers, polymeric multi-functional alcohols (polyols), and polyether polyols.

Still further examples of initiators include, but are not limited to, benzyl alcohol, ethyl glycolate, glycolic acid, lactic acid, hydroxybutyric acid, serine, threonine, serine-containing peptides, threonine-containing peptides, mannitol, sorbitol, glucose, fructose, sucrose, glucuronic acid, polyglycerol ethers containing from 1 to about 30 glycerol units, polyethylene glycols containing 1 to about 30 ethylene glycol units, and branched polyethylene glycols.

The ratio of monomers to initiator can be in the range of from about 30:1 to 1:1. For example, the ratio of monomer to initiator can be about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or 1:1. In one example, the ratio of monomer to initiator can be 21:1.

Secondary Components (or Agents)

The disclosed terpolymers compositions can also comprise one or more secondary components or agents. A secondary component is a bioactive agent, biomolecule, excipient, agent, modifier, surfactant, viscosity modifier, preservative, and/or adjuvant that is added to or admixed with the disclosed terpolymers. The secondary component can be covalently attached to the terpolymer, embedded within, or mixed into the terpolymer. The secondary component can be present during the synthesis of the terpolymer, but in most instances, the secondary component is added to the terpolymer composition after the terpolymer has been synthesized.

In many examples herein, the terpolymer compositions can have as a secondary component one or more bioactive agents (e.g., pharmaceutical (drug or vaccine), nutrient, biomolecule), contrast agent, imaging agent, dye, targeting moiety, synthetic polymer, magnetic particle, radioopacity agent, and the like. That is, the disclosed terpolymer compositions can be used as a carrier and delivery device for a wide variety of releasable bioactive agents having curative, therapeutic, or diagnostic value for human or non-human animals. Any of the bioactive agents described herein can be used in this respect. Many of these substances which can be carried by the disclosed compositions are discussed herein.

When the secondary component is a bioactive agent, it can be a drug or other pharmaceutically-active agent use to treat disease or illness. As such, agents including bioactive agents may be used to treat disease or illness in humans or in animals. Any such pharmaceutical can be used as a secondary component. Suitable examples of pharmaceuticals can be found in the Merck Index (13$^{th}$ Edition, Wiley, 2001), The United States Pharmacopeia-National Formulary (USP-NF), and the FDA's Orange book, which are each incorporated by reference herein at least for their teachings of pharmaceuticals. It is also contemplated that potential therapeutic agents including bioactive agents can be suitable secondary components in the disclosed terpolymer compositions. The resulting pharmaceutical-terpolymer compositions can provide a system for sustained, long-acting continuous delivery of drugs and other biologically-active agents to tissues adjacent to or distant from the application site. In many instances the pharmaceutical-terpolymer compositions are injectable. Classes of disease or illness that may be treated in such a manner include those found in "Goodman & Gilman's The Pharmacological Basis of Therapeutics" (McGraw-Hill, 9$^{th}$ Edition).

Suitable bioactive agents are capable of providing a local or systemic biological, physiological, or therapeutic effect in the biological system to which it is applied. For example, the bioactive agent can act to control infection or inflammation, enhance cell growth and tissue regeneration, control tumor growth, act as an analgesic, and promote anti-cell attachment, among other functions. Other suitable bioactive agents can include anti-viral agents, hormones, antibodies, or therapeutic proteins. Still other bioactive agents include prodrugs, which are agents that are not biologically active when administered but upon administration to a subject are converted to bioactive agents through metabolism or some other mechanism. Additionally, any of the compositions disclosed herein can contain combinations of two or more bioactive agents.

In some examples, the bioactive agents can include substances capable of preventing an infection systemically in the biological system or locally at the defect site, as for example, anti-inflammatory agents such as, but not limited to, pilocarpine, hydrocortisone, prednisolone, cortisone, diclofenac sodium, indomethacin, 6-methyl-prednisolone, corticosterone, dexamethasone, prednisone, and the like; analgesic agents including, but not limited to, salicylic acid, acetaminophen, ibuprofen, naproxen, piroxicam, flurbiprofen, morphine, and the like; local anesthetics including, but not limited to, lidocaine, benzocaine, bupivacaine, levobupivacaine, and the like; immunogens (vaccines) for stimulating antibodies against hepatitis, influenza, measles, rubella, tetanus, polio, rabies, and the like; peptides including, but not limited to, leuprolide acetate (an LH-RH agonist), nafarelin, and the like. Additionally, a substance or metabolic precursor that is capable of promoting growth and survival of cells and tissues or augmenting the functioning of cells is useful, as for example, a nerve growth promoting substance such as a ganglioside, a nerve growth factor, and the like; a hard or soft tissue growth promoting agent such as fibronectin (FN), human growth hormone (HGH), a colony stimulating factor, bone morphogenic protein, platelet-derived growth factor (PDGF), insulin-derived growth factor (IGF-I, IGF-II), transforming growth factor—α (TGF-α), transforming growth factor—β (TGF-β), epidermal growth factor (EGF), fibroblast growth factor (FGF), interleukin-1 (IL-1), vascular endothelial growth factor (VEGF) and keratinocyte growth factor (KGF), dried bone material, and the like; and antineoplastic agents such as methotrexate, 5-fluorouracil, adriamycin, vinblastine, cisplatin, tumor-specific antibodies conjugated to toxins, tumor necrosis factor, and the like.

Other useful bioactive agents include antibiotics such as acedapsone, acetosulfone sodium, alamecin, alexidine, amdinocillin, amdinocillin pivoxil, amicycline, amifloxacin, amifloxacin mesylate, amikacin, amikacin sulfate, aminosalicylic acid, aminosalicylate sodium, amoxicillin, amphomycin, ampicillin, ampicillin sodium, apalcillin sodium, apramycin, aspartocin, astromicin sulfate, avilamycini, avoparcin, azithromycin, azlocillin, azlocillin sodium, bacampicillin hydrochloride, bacitracin, bacitracin methylene disalicylate, bacitracin zinc, bambermycins, benzoylpas calcium, berythromycin, betamicin sulfate, biapenem, biniramycin, biphenamine hydrochloride, bispyrithione magsulfex, butikacin, butirosin sulfate, capreomycin sulfate, carbadox, carbenicillin disodium, carbenicillin indanyl sodium, carbenicillin phenyl sodium, carbenicillin potassium, carumonam sodium, cefaclor, cefadroxil, cefamandole, cefamandole nafate, cefamandole sodium, cefaparole, cefatrizine, cefazaflur sodium, cefazolin, cefazolin sodium, cefbuperazone, cefdinir, cefepime, cefepime hydrochloride, cefetecol, cefixime, cefmenoxime hydrochloride, cefmetazole, cefmetazole sodium, cefonicid monosodium, cefonicid sodium, cefoperazone sodium, ceforanide, cefotaxime sodium, cefotetan, cefotetan disodium, cefotiam hydrochloride, cefoxitin, cefoxitin sodium, cefpimizole, cefpimizole sodium, cefpiramide, cefpiramide sodium, cefpirome sulfate, cefpodoxime proxetil, cefprozil, cefroxadine, cefsulodin sodium, ceftazidime, ceftibuten, ceftizoxime sodium, ceftriaxone sodium, cefuroxime, cefuroxime axetil, cefuroxime pivoxetil, cefuroxime sodium, cephacetrile sodium, cephalexin, cephalexin hydrochloride, cephaloglycin, cephaloridine, cephalothin sodium, cephapirin sodium, cephradine, cetocycline hydrochloride, cetophenicol, chloramphenicol, chloramphenicol palmitate, chloramphenicol pantothenate complex, chloramphenicol sodium succinate, chlorhexidine phosphanilate, chloroxylenol, chlortetracycline bisulfate, chlortetracycline hydrochloride, cinoxacin, ciprofloxacin, ciprofloxacin hydrochloride, cirolemycin, clarithromycin, clinafloxacin hydrochloride, clindamycin, clindamycin hydrochloride, clindamycin palmitate hydrochloride, clindamycin phosphate, clofazimine, cloxacillin benzathine, cloxacillin sodium, cloxyquin, colistimethate sodium, colistin sulfate, coumermycin, coumermycin sodium, cyclacillin, cycloserine, dalfopristin, dapsone, daptomycin, demeclocycline, demeclocycline hydrochloride, demecycline, denofungin, diaveridine, dicloxacillin, dicloxacillin sodium, dihydrostreptomycin sulfate, dipyrithione, dirithromycin, doxycycline, doxycycline calcium, doxycycline fosfatex, doxycycline hyclate, droxacin sodium, enoxacin, epicillin, epitetracycline hydrochloride, erythromycin, erythromycin acistrate, erythromycin estolate, erythromycin ethylsuccinate, erythromycin gluceptate, erythromycin lactobionate, erythromycin propionate, erythromycin stearate, ethambutol hydrochloride, ethionamide, fleroxacin, floxacillin, fludalanine, flumequine, fosfomycin, fosfomycin tromethamine, fumoxicillin, furazolium chloride, furazolium tartrate, fusidate sodium, fusidic acid, gentamicin sulfate, gloximonam, gramicidin, haloprogin, hetacillin, hetacillin potassium, hexedine, ibafloxacin, imipenem, isoconazole, isepamicin, isoniazid, josamycin, kanamycin sulfate, kitasamycin, levofuraltadone, levopropylcillin potassium, lexithromycin, lincomycin, lincomycin hydrochloride, lomefloxacin, lomefloxacin hydrochloride, lomefloxacin mesylate, loracarbef, mafenide, meclocycline, meclocycline sulfosalicylate, megalomicin potassium phosphate, mequidox, meropenem, methacycline, methacycline hydrochloride, methenamine, methenamine hippurate, methenamine mandelate, methicillin sodium, metioprim, metronidazole hydrochloride, metronidazole phosphate, mezlocillin, mezlocillin sodium, minocycline, minocycline hydrochloride, mirincamycin hydrochloride, monensin, monensin sodiumr, nafcillin sodium, nalidixate sodium, nalidixic acid, natainycin, nebramycin, neomycin palmitate, neomycin sulfate, neomycin undecylenate, netilmicin sulfate, neutramycin, nifuiradene, nifuraldezone, nifuratel, nifuratrone, nifurdazil, nifurimide, nifiupirinol, nifurquinazol, nifurthiazole, nitrocycline, nitrofurantoin, nitromide, norfloxacin, novobiocin sodium, ofloxacin, onnetoprim, oxacillin sodium, oximonam, oximonam sodium, oxolinic acid, oxytetracycline, oxytetracycline calcium, oxytetracycline hydrochloride, paldimycin, parachlorophenol, paulomycin, pefloxacin, pefloxacin mesylate, penamecillin, penicillin G benzathine, penicillin G potassium, penicillin g procaine, penicillin g sodium, penicillin V, penicillin V benzathine, penicillin V hydrabamine, penicillin V potassium, pentizidone sodium, phenyl aminosalicylate, piperacillin sodium, pirbenicillin sodium, piridicillin sodium, pirlimycin hydrochloride, pivampicillin hydrochloride, pivampicillin pamoate, pivampicillin probenate, polymyxin B sulfate, porfiromycin, propikacin, pyrazinamide, pyrithione zinc, quindecamine acetate, quinupristin, racephenicol, ramoplanin, ranimycin, relomycin, repromicin, rifabutin, rifametane, rifamexil, rifamide, rifampin, rifapentine, rifaximin, rolitetracycline, rolitetracycline nitrate, rosaramicin, rosaramicin butyrate, rosaramicin propionate, rosaramicin sodium phosphate, rosaramicin stearate, rosoxacin, roxarsone, roxithromycin, sancycline, sanfetrinem sodium, sarmoxicillin, sarpicillin, scopafungin, sisomicin, sisomicin sulfate, sparfloxacin, spectinomycin hydrochloride, spiramycin, stallimycin hydrochloride, steffimycin, streptomycin sulfate, streptonicozid, sulfabenz, sulfabenzamide, sulfacetamide, sulfacetamide sodium, sulfacytine, sulfadiazine, sulfadiazine sodium, sulfadoxine, sulfalene, sulfamerazine, sulfameter, sulfamethazine, sulfamethizole, sulfamethoxazole, sulfamonomethoxine, sulfamoxole, sulfanilate zinc, sulfanitran, sulfasalazine, sulfasomizole, sulfathiazole, sulfazamet, sulfisoxazole, sulfisoxazole acetyl, sulfisboxazole diolamine, sulfomyxin, sulopenem, sultamricillin, suncillin sodium, talampicillin hydrochloride, teicoplanin, temafloxacin hydrochloride, temocillin, tetracycline, tetracycline hydrochloride, tetracycline phosphate complex, tetroxoprim, thiamphenicol, thiphencillin potassium, ticarcillin cresyl sodium, ticarcillin disodium, ticarcillin monosodium, ticlatone, tiodonium chloride, tobramycin, tobramycin sulfate, tosufloxacin, trimethoprim, trimethoprim sulfate, trisulfapyrimidines, troleandomycin, trospectomycin sulfate, tyrothricin, vancomycin, vancomycin hydrochloride, virginiamycin, and zorbamycin.

Still other useful bioactive agents include hormones such as progesterone, testosterone, and follicle stimulating hormone (FSH) (birth control, fertility-enhancement), insulin, and the like; antihistamines such as diphenhydramine, and the like; cardiovascular agents such as papaverine, streptokinase and the like; anti-ulcer agents such as isopropamide iodide, and the like; bronchodilators such as metaprotemal sulfate, aminophylline, and the like; vasodilators such as theophylline, niacin, minoxidil, and the like; central nervous system agents such as tranquilizer, B-adrenergic blocking agent, dopamine, and the like; antipsychotic agents such as risperidone, narcotic antagonists such as naltrexone, naloxone, buprenorphine; and other like substances. All of these agents are commercially available from suppliers such as Sigma Chemical Co. (Milwaukee, Wis.).

Included among bioactive agents that are suitable for incorporation into the disclosed compositions are therapeutic drugs, e.g., anti-inflammatory agents, anti-pyretic agents, steroidal and non-steroidal drugs for anti-inflammatory use, hormones, growth factors, contraceptive agents, antivirals, antibacterials, antibiotics, antifungals, analgesics, hypnotics, sedatives, tranquilizers, anti-convulsants, muscle relaxants, local anesthetics, anesthetics, antispasmodics, antiulcer drugs, peptidic agonists, sympathiomimetic agents, cardiovascular agents, antitumor agents, oligonucleotides and their analogues and so forth. The bioactive agent is added in pharmaceutically active amounts.

Further non-limiting examples of bioactive agents include, small molecule, a peptide, a protein, an enzyme (e.g., a kinase, a phosphatase, a methylating agent, a factor, a protease, a transcriptase, an endonuclease, a ligase, and the like), a vaccine, an antibody and/or fragment thereof, a nucleic acid (e.g., an oligonucleotide, a prime, a probe, an aptamer, a ribozyme, etc.), a lipid, a carbohydrate, a steroid, a hormone, a vitamin. In certain aspects, the bioactive agent can be a biomolecule (which are likely bioactive as well). Examples of biomolecules also include, but are not limited to, a small molecule, a peptide, a protein, an enzyme (e.g., a kinase, a phosphatase, a methylating agent, a factor, a protease, a transcriptase, an endonuclease, a ligase, and the like), a vaccine, an antibody and/or fragment thereof, a nucleic acid (e.g., an oligonucleotide, a prime, a probe, an aptamer, a ribozyme, etc.), a lipid, a carbohydrate, a steroid, a hormone, a vitamin. "Small molecule" as used herein, is meant to refer to a composition, which has a molecular weight of less than about 5 kD, for example, less than about 4 kD. Small molecules can be nucleic acids (e.g., DNA, RNA), peptides, polypeptides, peptidomimetics, carbohydrates, lipids, factors, cofactors, hormones, vitamins, steroids, trace elements, or other organic (carbon containing) or inorganic molecules. Such biomolecules can be obtained commercially or can be synthesized or isolated from natural sources by methods known in the art.

There are a variety of compositions disclosed herein where the secondary component (e.g., biomolecule) can comprise an amino acid based molecule, including for example peptides, proteins, enzymes, vaccines, and antibodies. Thus, as used herein, "amino acid," means the typically encountered twenty amino acids which make up polypeptides. Non-limiting examples of peptides include native peptides, synthetic peptides, biologically active peptides, factors, growth factors, and so on including, but not limited to, bioactive peptides and classes of bioactive peptides described in the "Handbook of Biologically Active Peptides" (A. J. Krastin, Editor; Academic Press, 2006).

In addition, it further includes less typical constituents which are both naturally occurring, such as, but not limited to formylmethionine and selenocysteine, analogs of typically found amino acids, and mimetics of amino acids or amino acid functionalities. Non-limiting examples of these and other molecules are discussed herein.

As used herein, the terms "peptide" and "protein" refer to a class of compounds composed of amino acids chemically bound together. Non-limiting examples of these and other molecules are discussed herein. In general, the amino acids are chemically bound together via amide linkages (CONH); however, the amino acids can be bound together by other chemical bonds known in the art. For example, the amino acids can be bound by amine linkages. "Peptide" as used herein includes oligomers of amino acids and small and large peptides, including naturally occurring or engineered polypeptides and proteins. It is understood that the terms "peptide" and "protein" can be used interchangeably herein.

Methods for producing such peptides and proteins are well known. One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant, Synthetic Peptides: A User Guide. W.H. Freeman and Co., N.Y. 1992; Bodansky and Trost, Ed. Principles of Peptide Synthesis. Springer-Verlag Inc., N.Y., 1993, which are incorporated by reference herein at least for their teachings of peptide synthesis).

In another example, the secondary component can comprise an antibody or fragment thereof. Antibodies or fragments thereof can be considered biomolecules, imaging agents, and/or target moieties, as the terms are used herein. The term "antibody" encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "antibody" as used herein is meant to include intact molecules as well as fragments thereof, such as, for example, Fab and F(ab')2, which are capable of binding the epitopic determinant. The term "antibody" also includes monoclonal and polyclonal antibodies, anti-idiopathic, and humanized antibodies.

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Such antibodies and fragments can be made by techniques known in the art (see Harlow and Lane. Antibodies, A Laboratory Manual. Cold Spring Harbor Publications, N.Y., 1988). Such antibodies and fragments thereof can be screened for specificity and activity according to the methods disclosed herein.

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference for at least its teaching of antibody conjugates. The fragments, whether attached to other sequences or not, include insertions, deletions, substitutions, or other selected modifications of particular regions or specific amino acid residues. Methods of producing and/or isolating antibodies as disclosed herein are well known.

There are also a variety of compositions disclosed herein where the secondary component can comprise a nucleic acid based molecule. Thus, as used herein, "nucleic acid" means a molecule made up of, for example, nucleotides, nucleotide analogs, or nucleotide substitutes. Non-limiting examples of these and other molecules are discussed herein. A nucleic acid can be double stranded or single stranded. Nucleic acid is also meant to include oligonucleotides, siRNA, DNA, plasmid, and the like.

As used herein, "nucleotide" is a molecule that contains a base moiety, a sugar moiety and a phosphate moiety. Nucleotides can be linked together through their phosphate moieties and sugar moieties creating an internucleoside linkage. The base moiety of a nucleotide can be adenine-9-yl (A), cytosine-1-yl (C), guanine-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

"Nucleotide analog," as used herein, is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

"Nucleotide substitutes," as used herein, are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Included herein are nucleic acid complexes or nucleic acid conjugates. It is also possible to link other types of molecules to nucleotides or nucleotide analogs to make conjugates or complexes that can enhance, for example, cellular uptake and cellular transfection. Conjugates or complexes can be chemically linked to the nucleotide or nucleotide analogs. Such conjugates include but are not limited to lipid moieties such as a cholesterol moiety (Letsinger et al., *Proc Natl Acad Sci USA*, 86:6553-6, 1989, which is incorporated by reference herein at least for its teachings of nucleic acid conjugates). Moreover, conjugates or complexes may be non-covalently associated by ionic or charge-charge or hydrophobic or by van der Waal's or by other non-covalent means. Examples of nucleic acid complexes or conjugates include nucleic acid polymer conjugates such as polyplexes in which the nucleic acid (such as a plasmid or DNA or siRNA) is covalently or non-covalently associated with a polymer. As used herein, the term nucleic acid includes such conjugates, complexes, analogs, polyplexes, and variants of nucleic acids.

Nucleic acids, such as those described herein, can be made using standard chemical synthetic methods or can be produced using enzymatic methods or any other known method. Such methods can range from standard enzymatic digestion followed by nucleotide fragment isolation (see for example, Sambrook et al., Molecular Cloning: A Laboratory Manual, 3d Edition, Cold Spring Harbor Laboratory Press, Cold Spring Harbor, N.Y., 2001, Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann Rev Biochem* 53:323-56, 1984, (phosphotriester and phosphite-triester methods), and Narang et al., *Methods Enzymol* 65:610-20, 1980, (phosphotriester method). Protein nucleic acid molecules can be made using known methods such as those described by Nielsen et al., *Bioconjug Chem*, 5:3-7, 1994. (Each of these references is incorporated by reference herein at least for their teachings of nucleic acid synthesis.)

Also, the secondary component can comprise an imaging agent, which is a chemical compound that can produce a detectable signal, either directly or indirectly. Many such imaging agents are known to those of skill in the art. Examples of imaging agents suitable for use in the disclosed compositions and method are radioactive isotopes, fluorescent molecules, magnetic particles (including nanoparticles), metal particles (including nanoparticles), phosphorescent molecules, enzymes, antibodies, and ligands. Imaging agents that combine two or more of the moieties disclosed herein are also considered imaging moieties.

Any of the known imaging agents can be used with the disclosed terpolymer compositions. Methods for detecting and measuring signals generated by imaging agents are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody.

In one example, the disclosed imaging agents can comprise a fluorescent imaging agent. A fluorescent imaging agent is any chemical moiety that has a detectable fluorescence signal. This imaging agent can be used alone or in combination with other imaging agents. Examples of suitable fluorescent agents that can be used in the compositions and methods disclosed herein include, but are not limited to, fluorescein (FITC), 5-carboxyfluorescein-N-hydroxysuccinimide ester, 5,6-carboxymethyl fluorescein, nitrobenz-2-oxa-1,3-diazol-4-yl (NBD), fluorescamine, OPA, NDA, indocyanine green dye, the cyanine dyes (e.g., Cy3, Cy3.5, Cy5, Cy5.5 and Cy7), 4-acetamido-4'-isothiocyanatostilbene-2,2'disulfonic acid, acridine, acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate, N-(4-anilino-1-naphthyl)maleimide, anthranilamide, BODIPY, Brilliant Yellow, coumarin, 7-amino-4-methylcoumarin (AMC, Coumarin 120), 7-amino-4-trifluoromethylcoumarin (Coumaran 151), cyanosine, 4',6-diaminidino-2-phenylindole (DAPI), 5',5"-dibromopyrogallol-sulfonaphthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansylchloride), 4-(4'-dimethylaminophenylazo)benzoic acid (DABCYL), 4-dimethylaminophenylazophenyl-4'-isothiocyanate (DABITC), eosin, eosin isothiocyanate, erythrosin B, erythrosine, isothiocyanate, ethidium bromide, ethidium, 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein isothiocyanate, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron[R] Brilliant Red 3B-A), 6-carboxy-X-rhodamine (ROX), 6-carboxyrhodamine (R6G), lissamine rhodamine B sulfonyl chloride rhodamine (Rhod), 5,6-tetramethyl rhodamine, rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, tetramethyl rhodamine isothiocyanate (TRITC), riboflavin, rosolic acid, coumarin-6, and the like, including combinations thereof. These fluorescent imaging moieties can be obtained from a variety of commercial sources, including Molecular Probes, Eugene, Oreg. and Research Organics, Cleveland, Ohio, or can be synthesized by those of ordinary skill in the art.

In another example, the disclosed imaging agents can comprise a Magnetic Resonance Imaging (MRI) agent. A MRI agent is any chemical moiety that has a detectable magnetic resonance signal or that can influence (e.g., increase or shift) the magnetic resonance signal of another agent. This type of imaging agent can be used alone or in combination with other imaging agent. In still another example, a gadolinium-based MRI agent can serve as an imaging agent. An example of a suitable MRI agent that can be incorporated into the disclosed imaging agents is para-amino-benzyl diethylenetriaminepentaacetic acid (p-$NH_2$-Bz-DTPA, Compound 7), a conjugable form of diethylenetriaminepentaacetic acid (DTPA), which is known to strongly bind gadolinium and is approved for clinical use as a magnetic resonance contrast agent. Others have successfully bound similar MRI contrast agents to PAM-AMTM (Kobayashi et al., *Bioconjugate Chem* 12:100-107, 2001; Kobayashi et al., *Mag Res in Medicine* 46:579-85, 2001) dendrimers for in vivo small animal imaging; these references are incorporated by reference herein at least for their teachings of MRI agents. Incorporation of an MRI agent on a large macromolecule such as a dendrimeric substrate as disclosed herein can allow large T1 relaxation (high contrast) and multiple copies of agent on a single molecule, which can increase signal. By combining an MRI imaging agent and, for example, a fluorescent imaging agent, the resulting agent can be detected, imaged, and followed in real-time via MRI.

Other imaging agents include PET agents that can be prepared by incorporating an 18F or a chelator for 64Cu or 68Ga. Also, addition of a radionuclide can be used to facilitate SPECT imaging or delivery of a radiation dose.

Plasticizers

The disclosed terpolymers can be used neat or they can be diluted with agents such as plasticizers to further reduce viscosity. That is, the viscosity of the disclosed terpolymer compositions can drop off with the addition of small quantities of plasticizers like biocompatible solvents (e.g., ethanol) as well as, lipids, plasticizers, additives (and the like), allowing further manipulation and control of viscosity (and, therefore, injectability) above and beyond that of the polymer itself. As such, the disclosed terpolymers compositions can comprise one or more plasticizers. Unlike the initiators disclosed herein, which are used to synthesize and become covalently attached end groups of the disclosed terpolymers, the disclosed plasticizers are not covalently bonded end groups.

Plasticizers should be biocompatible with and soluble in the terpolymer. Suitable plasticizers can be solvents, lipids, oils, fatty acids, surfactants, solubilizers, and polymeric additives. Examples of biocompatible solvents include fatty acids, oils, aromatic alcohols, lower alkyl esters of aryl acids, lower aralkyl esters of aryl acids, aryl ketones, aralkyl ketones, lower alkyl ketones, and lower alkyl esters of citric acid; benzoic acid derivatives; phthalic acid derivatives; and combinations thereof. Suitable examples of plasticizers include, but are not limited to, lactic acid, glycolic acid, hydroxybutyric acid, caprolactone, ethyl caproate, ethyl glycolate, ethyl oleate, benzyl benzoate, ethyl benzoate, lauryl lactate, benzyl alcohol, lauryl alcohol, glycofurol, ethyl acetate, ethanol, butanol, isopropyl alcohol, propanol, tocopherol, polyethylene glycol, triacetin, a triglyceride, an alkyltriglyceride, a diglyceride, rapeseed oil, sesame oil, peanut oil, castor oil, olive oil, cottonseed oil, perfluorocarbon, N-methyl pyrrolidone, N-methyl-2-pyrrolidinone, DMSO, glycerol, oleic acid, glycofurol, lauryl lactate, perfluorocarbon, propylene carbonate methyl benzoate, ethyl benzoate, n-propyl benzoate, isopropyl benzoate, butyl benzoate, isobutyl benzoate, sec-butyl benzoate, tert-butyl benzoate, isoamyl benzoate, benzyl benzoate, triethyl citrate, tributyl citrate, and combinations or mixtures thereof. Other examples include, but are not limited to, caprolactone, ethyl caproate, benzyl alcohol, ethyl acetate, acetone, butanone, methyl alcohol, butyl alcohol, methylene chloride, DMF, and the like, including mixtures thereof. Additional examples of plasticizers include, but are not limited to, glycerol triacetate, acetylated monoglycerides, citric acid esters, triethyl citrate, triethyl acetyl citrate, tributyl citrate, tributyl acetyl citrate, dibutyl phthalate, dibutyl sebacate, diethyloxalate, diethylmalate, diethylfumarate, diethylsuccinate, diethylmalonate, diethyltartrate, phthalic acid esters, diethylphthalate, dimethylphthalate, glycerin, glycerol, glyceryl triacetate, glyceryltributyrate, mineral oil and lanolin alcohols, petrolatum and lanolin alcohols, polyethylene glycols, propylene glycols, copolymers of polypropylene glycol and polyethylene glycol (including poloxamers), polyvinyl pyrrolidone, polysorbate 80, and the like, including mixtures thereof.

Plasticization of the terpolymers can be done by contacting a plasticizer to the polymer after the polymer is formed or by having the plasticizer present prior to and/or during polymer synthesis. In one specific example, the terpolymer is contacted with a plasticizing solvent by treating with solvent vapor or by placing the terpolymer directly into the plasticizing solvent liquid or into solutions that contain a plasticizer. In various examples, the plasticizers can be admixed with the viscous terpolymer in amounts of about 40 wt % or less, from about 30% or less, from about 20% or less, from about 15% or less, from about 10% or less, from about 5% or less of plasticizer, based on the total weight of the composition. For example, the compositions can comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, or 40% of plasticizer based on the total weight of the composition, where any of the stated values can form an upper or lower endpoint of a range.

Surfactants

Compositions comprising the disclosed terpolymers can also comprise agents such as surfactants. A "surfactant" as used herein is a molecule composed of hydrophilic and hydrophobic groups (i.e., an amphiphile). The surfactant can be an ionic or nonionic surfactant. For example, the disclosed terpolymer compositions can comprise an anionic surfactant. Any anionic surfactants can be used. Suitable anionic surfactants are commonly used in detergents, shampoos, soaps, etc., and can be obtained commercially or prepared by methods known in the art. They include, but are not limited to, alkylbenzene sulfonates (detergent), fatty acid based surfactants, lauryl sulfate (e.g., a foaming agent), di-alkyl sulfosuccinate (e.g., a wetting agent), lignosulfonates (e.g., a dispersant), and the like, including mixtures thereof. In other examples, linear alkylbenzene sulphonic acid, sodium lauryl ether sulphate, alpha olefin sulphonates, phosphate esters, sodium sulphosuccinates, hydrotropes, and the like, including mixtures thereof, can be used.

In other examples, the disclosed terpolymer compositions can comprise a cationic surfactant. Any cationic surfactant can be used. Suitable cationic surfactants included, but are not limited to, quaternary ammonium compounds, imidazolines, betaines, etc. Such cationic surfactants can be obtained commercially or can be prepared by methods known in the art.

In still other examples, the disclosed terpolymer compositions can comprise a nonionic surfactant. Any nonionic surfactant can be used. Suitable nonionic surfactants do not ionize in aqueous solution, because their hydrophilic group is of a non-dissociable type, such as alcohol, phenol, ether, ester, or amide. They can be classified as ethers (e.g., polyhydric alcohols such as glycerin, solbitole, sucrose, etc.), fatty acid esters (e.g., glycerin fatty acid ester, sobitan fatty acid ester, sucrose fatty acid ester, etc.), esters (e.g., compounds made by applying, for example, ethylene oxide to a material having hydroxyl radicals such as high alcohol, alkylphenol, and the like), ether/esters (e.g., compounds made by applying, for example, the ethylene oxide to the fatty acid or polyhydric alcohol fatty acid ester, having both ester bond and ether bond in the molecule), and other types (e.g., the fatty acid alkanol-amide type or the alkylpolyglyceride type). A particularly suitable nonionic surfactant is poly(vinyl alcohol). Other suitable examples of nonionic surfactants can include, but are not limited to, alcohol ethoxylates and alkyl phenol ethyoxylates, fatty amine oxides, alkanolamides, ethylene oxide/propylene oxide block copolymers, alkyl amine ethoxylates, tigercol lubricants, and the like, including mixtures thereof.

In yet other examples, the disclosed terpolymer compositions can comprise dipolar surfactants. Any dipolar surfactant can be used. Suitable dipolar surfactants (called amphoteric or zwitterionic) exhibit both anionic and cationic dissociation. Suitable examples of dipolar surfactants include, but are not limited to, products like betaines or sulfobetaines and natural substances such as amino acids and phospholipids. In one example, the betaines disclosed in U.S. Pat. Nos. 6,852, 816; 6,846,795; 6,846,352; and 6,849,426, which are incorporated by reference in their entireties, can be used herein.

Other examples of suitable surfactants include natural surfactants, which can have their source from plant or animal organs. In another example, a boloform surfactant can be used. A boloform surfactant is a surfactant that has two hydrophilic head groups at opposite ends of a hydrophobic tail.

Mixtures of these surfactants can also be used in the compositions and methods disclosed herein.

Additives

Compositions comprising the disclosed terpolymers can also comprise other agents including additives or excipients. For example, the disclosed terpolymer compositions can contain pH buffers, organic acids (e.g., formic, acetic, propionic, benzoic, maleic, oxalic acids, and the like), mineral acids (e.g., HCl, HBr, $H_2SO_4$, $H_3PO_4$, and the like), bases (e.g., NaOH, KOH, $Et_3N$, $Na_2CO_3$, $NaHCO_3$, $KHCO_3$, and the like), preservatives, dyes, antioxidants (e.g., ascorbic acid and tocopherols), wetting, emulsifying, suspending agents, flocculating, and dispensing agents.

The disclosed terpolymer compositions can also contain other additives for preventing the action of microorganisms. This can be accomplished by various antimicrobial and/or antifungal agents, for example, parabens, chlorobutanol, phenol, sorbic acid, quaternary ammonium compounds, and the like.

It may also be desirable to include binders such as carboxymethylcellulose, alignates, gelatin, polyvinyl pyrrolidone, sucrose, and acacia, humectants such as glycerol, wetting agents such as cetyl alcohol and glycerol monostearate, adsorbents such as kaolin and bentonite, and lubricants such as talc, calcium stearate, magnesium stearate, polyethylene glycols, polypropylene glycols, copolymers of polyethylene glycol and polypropylene glycol, sodium lauryl sulfate, or mixtures thereof.

Suitable flocculating agents that can be used include, but are not limited to, aluminum salts (e.g., aluminium sulphate), ferrous salts, and ferric salts (e.g., ferric sulphate and ferric chloride). Suitable suspending agents can include, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. The disclosed terpolymer compositions can also comprise solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Further, the disclosed terpolymers can be combined with an aqueous diluent to result in polymeric micelles of the terpolymer. The composition can be processed (e.g., by passing through a sieve or by passing through a filter or by vigorous stirring or by sonication) to facilitate micelle formation. Additionally, the disclosured terpolymer can be first dissolved in one solvent (for example, the water-soluble and volatile solvent acetone) which is then slowly added to the aqueous vehicle before it is removed by evaporation or by distillation (under reduced pressure) to form the polymer micelle in the aqueous diluent. The terpolymer micelles can be from about 1 to about 1000 nm, from about 1 to about 150 nm, from about 1 to about 100 nm, from about 1 to about 10 nm, from about 25 to about 100 nm, from about 10 to about 75 nm, or from about 10 to about 50 nm in diameter. The polymer micelle composition can be combined with any of the stated bioactive agents disclosed herein, especially hydrophobic bioactive agents.

Uses

The disclosed terpolymer compositions have many uses, most notably is the use of these viscous polymers for local and systemic drug delivery. For example, compositions where a bioactive agent (i.e., secondary component) is incorporated into neat, viscous terpolymers as disclosed herein can be administered to a subject orally, by injection, or by implantation. In such a case, the bioactive agent can be dissolved in the terpolymer composition or suspended within the terpolymer composition, or both depending on the solubility and loading level of the drug in the terpolymer composition. Alternatively, the disclosed viscous terpolymers can be plasticized through the addition of a plasticizer (such as a solvent) to lower the viscosity of the viscous polymer and/or to alter the solubility of the bioactive agent in the polymer and/or to alter the bioactive agent release characteristics from the polymer. Plasticizing the terpolymers with a plasticizer can occur prior to, during, or after incorporating the bioactive agent into the terpolymer. For example, the bioactive agent can be admixed with the plasticizer and then the combination admixed with the terpolymer. Or, the terpolymer can be plasticized and the bioactive agent is subsequently added. Still further, the terpolymer and be plasticized with one plasticizer and the bioactive agent can be combined with the same or different plasticizer, which are then combined with the plasticized terpolymer. As noted, plasticizer can affect viscosity of the system to change the administration characteristics (for example, to permit administration by injection) or to otherwise affect drug solubility or the drug release characteristics following administration.

Another method is to blend the neat terpolymer into other biodegradable and biocompatible polymers to alter the properties of those other polymers (such as by lowering the Tg of the final polymer admixture). Such other biodegradable and biocompatible polymers are known and commercially available.

Depending on the particular bioactive agent, any of these methods can be used for any/all classes of treatments (including pain, anesthesia, orthopaedic applications, soft tissue repair or replacement, hard tissue repair or replacement, cancer, CNS disorders, and the like as referenced previously in "Goodman & Gilman's The Pharmacological Basis of Therapeutics" (McGraw-Hill, $9^{th}$ Edition). That is, because the disclosed terpolymers can be formulated with any bioactive agent into an oral, injectable, or implantable composition, any disease or injury.

Dosage

When used in the above described methods or other treatments, or in the pharmaceutical formulations (e.g., a terpolymer composition as disclosed herein with a bioactive agent) disclosed herein, an "effective amount" of one of the disclosed bioactive agents can be employed in pure form or, where such forms exist, in pharmaceutically acceptable salt form, and with or without a pharmaceutically acceptable excipient, carrier, or other additive.

The specific effective amount for any particular subject will depend upon a variety of factors including the disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts. For example, it is well within the skill of the art to start doses of a composition at levels lower than those required to achieve the desired therapeutic effect and to gradually increase the dosage until the desired effect is achieved. One can also evaluate the particular aspects of the medical history, signs, symptoms, and objective laboratory tests that are known to be useful in evaluating the status of a subject in need of attention for the treatment of ischemia-reperfusion injury, trauma, drug/toxicant induced injury, neurodegenerative disease, cancer, or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved (e.g., a tumor has partially or fully regressed), 2) the progression of the disease or condition is shown to be stabilized, or slowed, or reversed, or 3) the need for other medications for treating the disease or condition is lessened or obviated, then a particular treatment regimen will be considered efficacious. If desired, the effective daily dose can be divided into multiple doses for purposes of administration. Consequently, single dose compositions can contain such amounts or submultiples thereof to make up the daily dose.

In a further aspect, an effective amount can be determined by preparing a series of compositions comprising varying amounts of bioactive agents and determining the release characteristics in vivo and in vitro and matching these characteristics with specific pharmaceutical delivery needs, inter alia, subject body weight, disease condition and the like.

The dosage can be adjusted by the individual physician or the subject in the event of any counterindications. Dosage can vary, and can be administered in one or more dose administrations daily, for one or several days. Guidance can be found in the literature for appropriate dosages for given classes of pharmaceutical products.

Pharmaceutical Formulations

Also, pharmaceutical formulations comprising the disclosed terpolymers and one or more bioactive agents are disclosed herein. A suitable pharmaceutical formulation can comprise any of the disclosed terpolymers and bioactive agents, along with a pharmaceutically acceptable carrier. In many examples, the terpolymers disclosed herein are themselves pharmaceutically acceptable carriers. The pharmaceutical formulations disclosed herein can be used therapeutically or prophylactically.

By "pharmaceutically acceptable" is meant a material that is not biologically or otherwise undesirable, i.e., the material may be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Suitable carriers and their formulations are described in *Remington: The Science and Practice of Pharmacy*, 21$^{st}$ Ed., Lippincott Williams & Wilkins, Philadelphia, Pa., 2005, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8 (e.g., from about 7 to about 7.5). Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, marine oils, and injectable organic esters such as ethyl oleate. Aqueous carriers include water, alcoholic/aqueous solutions, and emulsions or suspensions, including saline and buffered media. Parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations for topical administration may include ointments, lotions, creams, gels, drops, suppositories, sprays, liquids and powders. Conventional pharmaceutical carriers, aqueous, powder or oily bases, thickeners and the like can be desirable.

Pharmaceutical formulations for oral administration include, but are not limited to, powders or granules, suspensions or solutions in water or non-aqueous media, capsules, gel-caps, sachets, or tablets. Thickeners, flavorings, diluents, emulsifiers, dispersing aids, or binders can be desirable.

Some of the formulations can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, pamoic acid and fumaric acid, or by reaction with an inorganic base such as sodium hydroxide, ammonium hydroxide, potassium hydroxide, and organic bases such as mono-, di-, trialkyl and aryl amines and substituted ethanolamines.

Pharmaceutical Kits

Also disclosed are kits or packages of pharmaceutical formulations designed for use in the regimens described herein. These kits can be designed for daily oral delivery over 4-hour, 6-hour, 8-hour, 12-hour, 24-hour, 48-hour, 72-hour, 7-day, 10-day, 21-day, or 30-day cycle, among others, and also for one oral delivery per day. When the compositions are to be delivered continuously, a package or kit can include the composition in each tablet. When the compositions are to be delivered with periodic discontinuation, a package or kit can include placebos on those days when the composition is not delivered.

The kits can also be organized to indicate a single oral formulation or combination of oral formulations to be taken on each day of the cycle, including oral tablets to be taken on each of the days specified, for example, one oral tablet will contain each of the combined daily dosages indicated.

In one example, a kit can include a single phase of a daily dosage of the disclosed compounds over a 4-hour, 6-hour, 8-hour, 12-hour, 24-hour, 48-hour, 72-hour, 7-day, 10-day, 21-day, or 30-day cycle.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, pH, etc.) but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, temperatures, pressures, and other reaction ranges and conditions that can be used to optimize the product purity and yield obtained from the described process. Only reasonable and routine experimentation will be required to optimize such process conditions.

Certain materials, compounds, compositions, and components disclosed herein can be obtained commercially or readily synthesized using techniques generally known to those of skill in the art. For example, the starting materials and reagents used in preparing the disclosed compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplements (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Specific Methods

The following analytical methods were used in all examples, unless indicated otherwise.

The inherent viscosity (IV; dL/g) was measured at 0.5% (wt/vol) terpolymer in chloroform at 30° C. using a Cannon-Fenske size 25 viscometer.

Polymer composition was determined from $^1$H-NMR spectra recorded in $CDCl_3$ on a Varian Inova spectrometer at 399.85 MHz.

Thermal properties were determined using a TA Instruments Differential Scanning Calorimeter (DSC) 2920 with Refrigerated Cooling System (RCS). The thermal history was removed by an initial heat ramp. The glass transition temperature ($T_g$) is determined from the DSC curve obtained from a temperature scan rate of 10° C./minute over a temperature range of about −60° C. to 90° C.

Gel permeation chromatography (GPC) analyses were performed on a Perkin Elmer Series 200 GPC/RI fitted with a Waters Styragel HR-2 and two Waters HR-5E columns, using chloroform as the mobile phase, and calibrated with multiple polystyrene standards of narrow molecular weight distribution. Molecular weights are reported in Daltons for the weight-average (Mw) and the number-average (Mn) molecular weights. The polydispersity index (PDI) is simply the ratio of Mw divided by Mn and is an indicator of the molecular weight distribution.

Rheological experiments were conducted on an AR2000 rheometer (TA Instruments Inc, Delaware) using a parallel plate geometry with a 1 mm gap. Samples were subjected to steady shear forces with the shear rate increasing stepwise from 0.1 to 1000 reciprocal seconds (1/s). The viscosity, $\eta$, versus shear rate was recorded. Viscosity measurements were conducted at room temperature (19-22° C.). The viscosity reported from rheological measurements is defined as the average viscosity of the material over the range where viscosity is observed to be independent of the shear rate (FIG. 1). This is an average viscosity value for a particular sample that excludes any shear-thinning effects.

Oscillatory rheology measurements were also conducted using an AR2000 rheometer (TA Instruments Inc, Delaware) using a parallel plate geometry with a 1 mm gap at room temperature (19-22° C.). These experiments were conducted by applying oscillatory shear forces to the samples and measuring their response. The controlled variable was percent strain, kept at 1.0. The angular frequency was increased from 0.1 to 100 radians per second (rad/sec) for the oscillatory experiment. The phase difference between the input and the response was used to calculate the storage, modulus (G'), the loss modulus (G"), the phase angle, delta ($\delta$), and the dynamic viscosity ($\eta$').

A Brookfield Model RVTD viscometer was used with a UL (low viscosity) adapter to measure rotational viscosity of a terpolymer composition using a rotational speed of 20 rpm. Measurements were performed at room temperature (19-20° C.).

In the following examples, terpolymer compositions are indicated by a numerical designation which indicates the mole ratio composition of lactide, glycolide, and caprolactone (respectively) in the terpolymer. Letter designations refer to the monomers in the terpolymer where DL refers to DL-lactide, L refers to L-lactide, G refers to glycolide and CL refers to caprolactone. Subsequent nomenclature indicates the initiator species and the end-group composition where the letter designation E specifies that the polymer chains are terminated with an ester end-group. For example, a terpolymer described as 271954 DLGCL-(1-dodecanol)-E consists of a terpolymer containing a mole ratio of approximately 27% DL-lactide, 19% glycolide, and 54% caprolactone that was initiated with 1-dodecanol and contains an ester-terminated end-group (Example 1 terpolymer).

Example 1

271954 DLGCL 1-(1-Dodecanol)-E

A thoroughly dried resin kettle equipped with a nitrogen inlet, air-cooled distillation adapter with trap, and mechanical stirrer was charged with 105.0 grams (0.728 mol) of DL-lactide (Ortec, South Carolina) and 56.4 grams (0.486 mol) of glycolide (Ortec, South Carolina). The monomer was blanketed with nitrogen and melted at 140° C. 138.6 grams (1.214 mol) of ε-caprolactone (Ortec, South Carolina) and 21.3 grams (0.114 mol) of the initiator 1-dodecanol (Sigma-Aldrich, Wisconsin) was added. After thorough mixing, the mixture was charged with 96.6 milligrams (0.239 mmol) of the catalyst stannous octoate (Sigma-Aldrich, Wisconsin). The polymerization proceeded for 18 hours at 160° C. followed by a 2 hour vacuum strip at 28.5 in HG vacuum to remove un-reacted monomer. DL-lactide:glycolide:ε-caprolactone mole ratio=27:19:54; IV=0.13 dL/g; $T_g$=−31.4° C.; $M_w$=9,900, $M_n$=5,200, polydispersity index (PDI=1.9).

Example 2

272152 DLGCL 1-(Ethyl Glycolate)-E

The terpolymer was prepared according to the method of Example 1 using 11.9 grams (0.114 mol) of the initiator ethyl glycolate (Sigma-Aldrich, Wisconsin) and 96.4 milligrams (0.238 mmol) of the catalyst stannous octoate (Sigma-Aldrich, Wisconsin). DL-lactide:glycolide:ε-caprolactone mole ratio=27:21:52; IV=0.15 dL/g; $T_g$=−23.2° C.; $M_w$=10,000, $M_n$=4,000 (PDI=2.6).

Example 3

271954 DLGCL 1-(Oleyl Alcohol)-E

The terpolymer was prepared according to the method of Example 1 using 30.7 grams (0.114 mol) of the initiator oleyl alcohol (Sigma-Aldrich, Wisconsin) and 103.0 milligrams (0.2544 mmol) of the catalyst stannous octoate (Sigma-Aldrich, Wisconsin). DL-lactide:glycolide:ε-caprolactone mole ratio=27:19:54; IV=0.14 dL/g; $T_g$=−35.4° C.; $M_w$=11,000 and $M_n$=6,000 (PDI=1.8).

Example 4

271954 DLGCL 1-(Glycerol)-E

The terpolymer was prepared according to the method of Example 1 using 10.6 grams (0.115 mol) of the initiator glycerol (Sigma-Aldrich, Wisconsin) and 93.7 milligrams (0.231 mmol) of the catalyst stannous octoate (Sigma-Aldrich, Wisconsin). DL-lactide:glycolide:ε-caprolactone mole ratio=27:19:54; IV=0.11 dL/g; $T_g$=−22.8° C.; $M_w$=7,600, $M_n$=5,200 (PDI 1.5).

Example 5

281953 DLGCL 1-(mPEG 350)-E

The terpolymer was prepared according to the method of Example 1 using 40.3 grams (0.114 mol) of the initiator poly(ethylene glycol) methyl ether (mPEG 350, Sigma-Aldrich, Wisconsin) and 102.8 milligrams (0.2538 mmol) of the catalyst stannous octoate (Sigma-Aldrich, Wisconsin). DL-lactide:glycolide:ε-caprolactone mole ratio=28:19:53; IV=0.14 dL/g; $T_g$=−32.4° C.; $M_w$=9,300 and $M_n$=3,800 (PDI=2.4).

Example 6

302050 DLGCL 1-(12:0-PEG)-E

The terpolymer was prepared according to the method of Example 1 using 40.9 grams (0.114 mol) of the initiator PEG-400 monolaurate (Sigma-Aldrich, Wisconsin) and 102.8 milligrams (0.2538 mmol) of the catalyst stannous octoate (Sigma-Aldrich, Wisconsin). DL-lactide:glycolide:ε-caprolactone mole ratio=30:20:50; IV=0.19 dL/g; $T_g$=−28.9° C.; $M_w$=16,000 and $M_n$=6,300 (PDI=2.5).

Example 7

281953 DLGCL 1-(1-ethyl-2-hexanoate)-E

The terpolymer was prepared according to the method of Example 1 using 15.0 grams (0.115 mol) of the initiator 1-ethyl-2-hexanol (Sigma-Aldrich, Wisconsin) and 94.0 milligrams (0.232 mmol) of the catalyst stannous octoate (Sigma-Aldrich, Wisconsin). DL-lactide:glycolide:ε-caprolactone mole ratio=28:19:53; IV=0.15 dL/g; $T_g$=−28.6° C.; $M_w$=11,000 and $M_n$=6,100 (PDI=1.8).

Example 8

162658 DLGCL 1-(1-Dodecanol)-E

The terpolymer was prepared according to the method of Example 1 using 72.0 grams (0.500 mol) of DL-lactide (Ortec, South Carolina), 86.1 grams (0.742 mol) of glycolide (Ortec, South Carolina), 142.1 grams (1.24 mol) of ε-caprolactone (Ortec, South Carolina), 42.9 grams (0.230 mol) of the initiator 1-dodecanol (Sigma-Aldrich, Wisconsin) and 110 milligrams (0.272 mmol) of the catalyst stannous octoate (Sigma-Aldrich, Wisconsin). DL-lactide:glycolide:ε-caprolactone mole ratio=16:26:58; IV=0.10 dL/g; $T_g$=−43.8° C.; $M_w$=4,800 and $M_n$=2,500 (PDI 1.9).

Example 9

442828 DLGCL 1-(1-Dodecanol)-E

The terpolymer was prepared according to the method of Example 1 using 166.4 grams (1.155 mol) of DL-lactide (Ortec, South Carolina), 80.6 grams (0.694 mol) of glycolide (Ortec, South Carolina), 52.8 grams (0.463 mol) of ε-caprolactone (Ortec, South Carolina), 40.1 grams (0.215 mol) of the initiator 1-dodecanol (Sigma-Aldrich, Wisconsin) and 107 milligrams (0.264 mmol) of the catalyst stannous octoate (Sigma-Aldrich, Wisconsin). DL-lactide:glycolide:ε-caprolactone mole ratio=44:28:28; IV=0.08 dL/g; $T_g$=0.56° C.; $M_w$=4,500 and $M_n$=2,400 (PDI 1.9).

Example 10

502030 DLGCL 1-(1-Dodecanol)-E

The terpolymer was prepared according to the method of Example 1 using 184.6 grams (1.281 mol) of DL-lactide (Ortec, South Carolina), 58.3 grams (0.502 mol) of glycolide (Ortec, South Carolina), 57.3 grams (0.502 mol) of ε-caprolactone (Ortec, South Carolina), 39.5 grams (0.212 mol) of the initiator 1-dodecanol (Sigma-Aldrich, Wisconsin) and 106 milligrams (0.263 mmol) of the catalyst stannous octoate (Sigma-Aldrich, Wisconsin). DL-lactide:glycolide:ε-caprolactone mole ratio=50:20:30; IV=0.09 dL/g; $T_g$=−13.5° C.; $M_w$=4,500 and $M_n$=2,400 (PDI 1.9).

Example 11

312049 DLGCL 1-(1-Dodecanol)-E

The terpolymer was prepared according to the method of Example 1 using 124.6 grams (0.864 mol) of DL-lactide (Ortec, South Carolina), 61.1 grams (0.526 mol) of glycolide (Ortec, South Carolina), 114.7 grams (1.005 mol) of ε-caprolactone (Ortec, South Carolina), 41.3 grams (0.222 mol) of the initiator 1-dodecanol (Sigma-Aldrich, Wisconsin) and 103 milligrams (0.255 mmol) of the catalyst stannous octoate (Sigma-Aldrich, Wisconsin). DL-lactide:glycolide:ε-caprolactone mole ratio=31:20:49, IV=0.09 dL/g; $T_g$=−35.4° C.; $M_w$=4,800 and $M_n$=2,500 (PDI 1.9).

Example 12

152956 LGCL 1-(1-Dodecanol)-E

A glass reactor was equipped with a magnetic stir bar was charged with 6.0 grams (0.041 mol) of L-lactide (Ortec, South Carolina), 7.7 grams (0.066 mol) of glycolide (Ortec, South Carolina), 11.3 grams (0.994 mol) of ε-caprolactone (Ortec, South Carolina) and 3.6 grams (0.019 mol) of 1-dodecanol (Sigma-Aldrich, Wisconsin). The reaction was purged with nitrogen and the contents melted at 140° C. after which 9 milligrams (0.02 mmol) of the catalyst stannous octoate (Sigma-Aldrich, Wisconsin) was added. The polymerization proceeded for 18 hours at 160° C. followed by a 2 hour vacuum strip at 28.5 in HG vacuum to remove un-reacted monomer. L-lactide:glycolide:ε-caprolactone mole ratio=15:29:56; IV=0.10 dL/g; $T_g$=−41.5° C.; $M_w$=5,100 and $M_n$=2,900 (PDI 1.7).

Example 13

232651 DLGCL 1-(Oleyl Alcohol)-E

The terpolymer was prepared according to the method of Example 12 using 6.0 grams (0.041 mol) of DL-lactide (Ortec, South Carolina), 7.7 grams (0.066 mol) of glycolide (Ortec, South Carolina), 11.3 grams (0.992 mol) of ε-caprolactone (Ortec, South Carolina), 5.2 grams (0.019 mol) of oleyl alcohol (Sigma-Aldrich, Wisconsin) and 9 milligrams (0.02 mmol) of the catalyst stannous octoate (Sigma-Aldrich, Wisconsin). DL-lactide:glycolide-caprolactone mole ratio of 23:26:51; IV=0.09 dL/g; $T_g$=−44.4° C.; $M_w$=4,700 and $M_n$ 2,400 (PDI 2.0).

Example 14

163153 DLGCL 1-(Ethyl Glycolate)-E

The terpolymer was prepared according to the method of Example 12 using 6.0 grams (0.041 mol) of DL-lactide (Ortec, South Carolina), 7.7 grams (0.066 mol) of glycolide (Ortec, South Carolina), 11.3 grams (0.992 mol) of ε-caprolactone (Ortec, South Carolina), 2.0 grams (0.019 mol) of ethyl glycolate (Sigma-Aldrich, Wisconsin) and 9 milligrams (0.02 mmol) of the catalyst stannous octoate (Sigma-Aldrich, Wisconsin) at 60° C. followed by a 2 hour vacuum strip at 28.5 in HG vacuum to remove un-reacted monomer. DL-lactide:glycolide:ε-caprolactone mole ratio of 16:31:53; IV=0.11 dL/g; $T_g$=−27.5° C.; $M_w$=5,700 and $M_n$=2,700 (PDI 2.1).

Refer to Table 2 for a listing of samples prepared in the preceeding Examples. Copolymer compositions are identified by the mole ratio of lactide (L), glycolide (G), and caprolactone (CL) in the final polymer. Table 2 also includes the inherent viscosity (IV), glass transition temperature (Tg), and the weight-average (Mw) and number-average (Mn) molecular weights.

TABLE 2

Description and attributes of terpolymer samples from Examples 1 to 14.
Terpolymer Examples

| Example No. | Initiator | Actual mole ratio, L:G:CL | IV, dL/g | Tg, ° C. | Mw, Da | Mn, Da | PDI |
|---|---|---|---|---|---|---|---|
| 1 | 1-dodecanol | 27:19:54 | 0.13 | −31.4 | 9,900 | 5,200 | 1.9 |
| 2 | Ethyl glycolate | 27:21:52 | 0.15 | −23.2 | 10,000 | 4,000 | 2.6 |
| 3 | Oleyl alcohol | 27:19:54 | 0.14 | −35.4 | 11,000 | 6,000 | 1.8 |
| 4 | Glycerol | 27:19:54 | 0.11 | −22.8 | 7,600 | 5,200 | 1.5 |
| 5 | mPEG-350 | 28:19:53 | 0.14 | −32.4 | 9,300 | 3,800 | 2.4 |
| 6 | Monolauryl-PEG-400 | 30:20:50 | 0.19 | −28.9 | 16,000 | 6,300 | 2.5 |
| 7 | 1-ethyl-2-hexanol | 28:19:53 | 0.15 | −28.6 | 11,000 | 6,100 | 1.8 |
| 8 | 1-dodecanol | 16:26:58 | 0.10 | −43.8 | 4,800 | 2,500 | 1.9 |
| 9 | 1-dodecanol | 44:28:28 | 0.08 | 0.56 | 4,500 | 2,400 | 1.9 |
| 10 | 1-dodecanol | 50:20:30 | 0.09 | −13.5 | 4,500 | 2,400 | 1.9 |
| 11 | 1-dodecanol | 31:20:49 | 0.09 | −35.4 | 4,800 | 2,500 | 1.9 |
| 12 | 1-dodecanol | 15:29:56 | 0.10 | −41.5 | 5,100 | 2,900 | 1.7 |
| 13 | Oleyl alcohol | 23:26:51 | 0.09 | −44.4 | 4,700 | 2,400 | 2.0 |
| 14 | Ethyl glycolate | 16:31:53 | 0.11 | −27.5 | 5,700 | 2,700 | 2.1 |

Example 15

Stepped-Shear Viscosity Testing

The viscosity reported from rheological measurements is defined as the average viscosity of the material where viscosity is observed to be independent of the shear rate (FIG. 1). This is an average viscosity value for a particular sample that excludes any shear-thinning effects.

FIG. 1 is a graph showing an example plot of stepped-shear viscosity versus shear rate. The highlighted data points show the region where viscosity is independent of shear rate from which the reported viscosity value is estimated.

Figure 2:
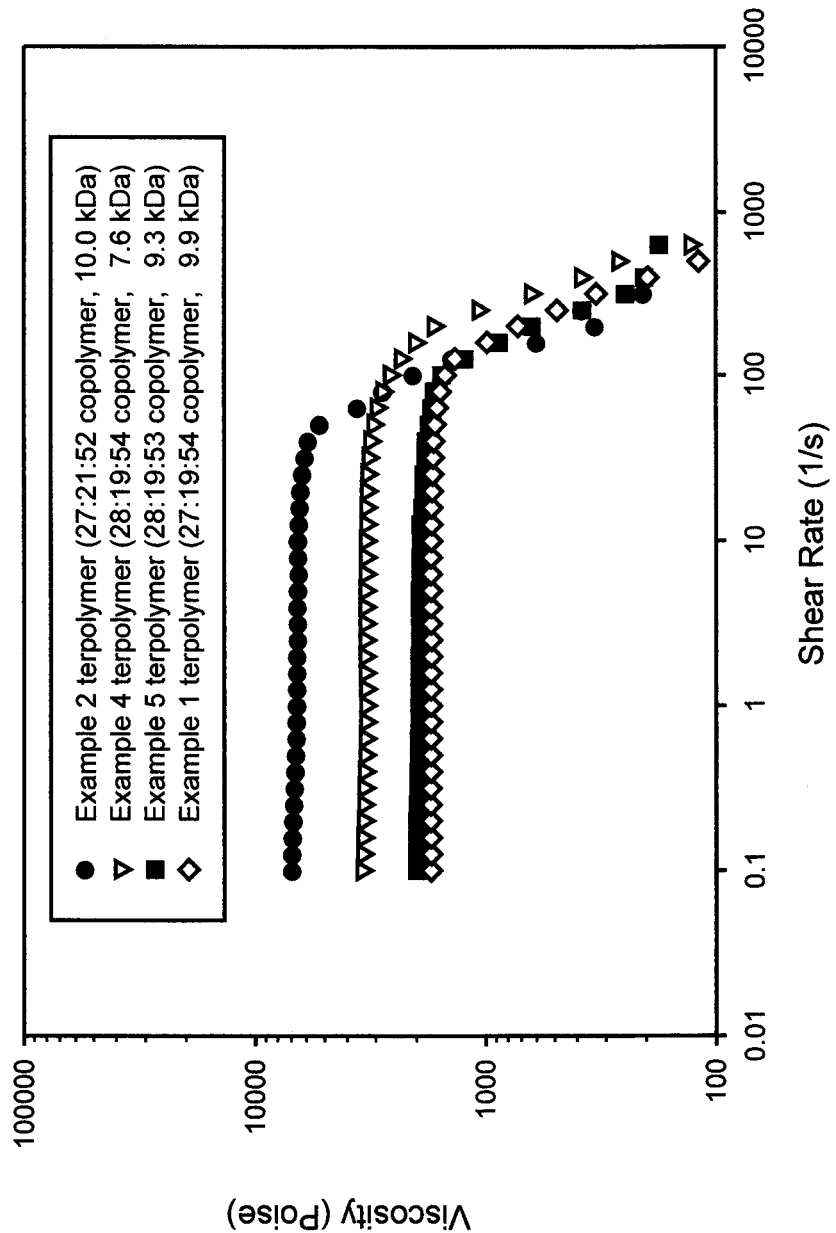
FIG. 2 is a graph of viscosity (poise) versus shear rate (sec$^1$) data from terpolymers of similar molecular weight and composition that were prepared using different initiators.

FIG. 2 is a graph showing viscosity-shear rate results from high molecular weight terpolymers prepared using different initiators. These terpolymer samples have similar monomer compositions (approximately 30:20:50 mole ratios of L:G:CL) and molecular weights (weight-average molecular weights ranging from about 7.6 to 11.0 kD). In these examples, viscosities range from about 1,700-6,500 poise depending, largely, on the choice of initiator.

Figure 3:
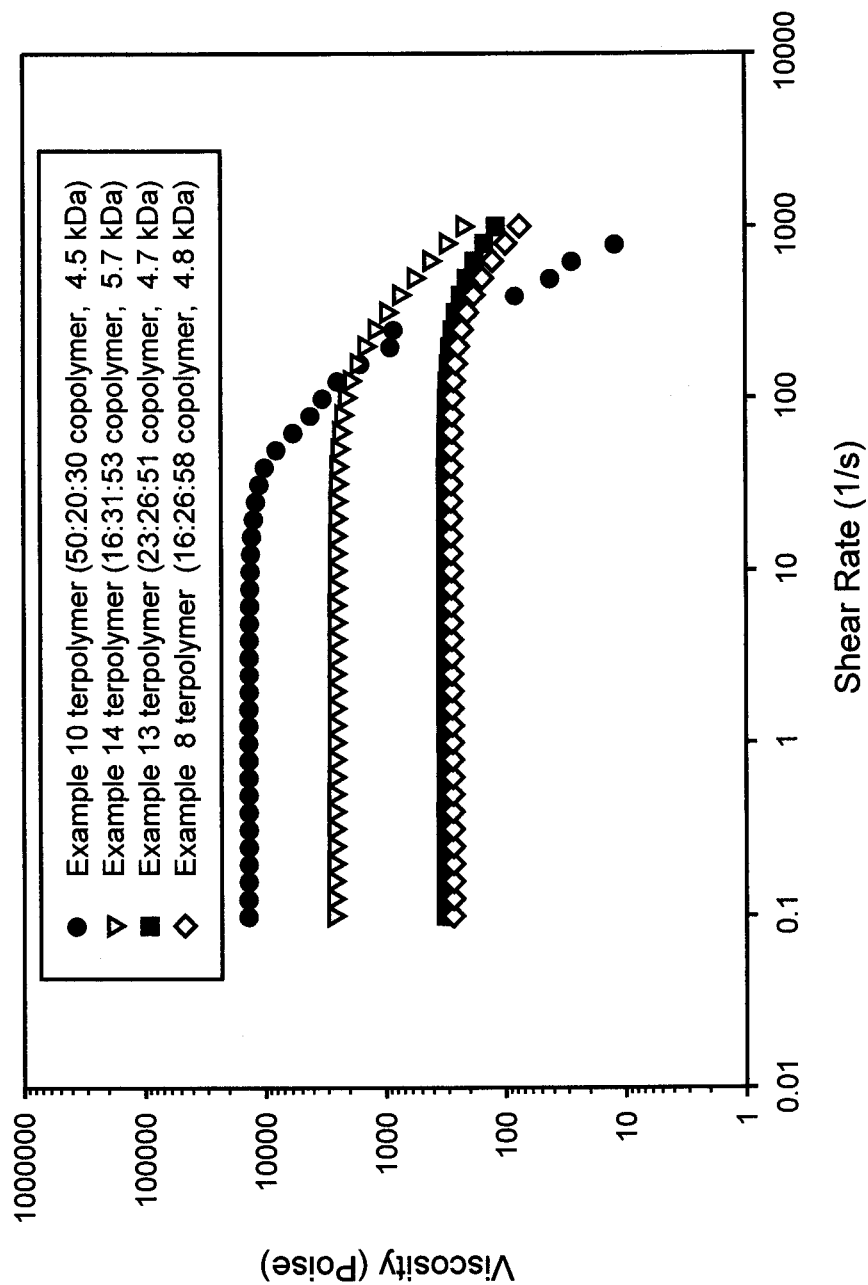
FIG. 3 is a graph of viscosity (poise) versus shear rate (sec$^{-1}$) data from low molecular weight terpolymers prepared with different initiators and monomer composition.

FIG. 3 shows viscosity-shear rate results for relatively low molecular weight terpolymers prepared using different initiators and containing different monomer compositions. Initiator effects on viscosity are demonstrated by comparison of Example 14 (ethyl glycolate initiator) and Example 8 (1-dodecanol initiator) where viscosities of 2,640 poise and 282 poise (respectively) were observed. Also demonstrated in FIG. 3 are effects of copolymer composition on viscosity. Examples 8 and 10 were both prepared using 1-dodecanol as the initiator; markedly lower viscosity was observed in the copolymer composition containing the higher composition of caprolactone and low levels of lactide (namely, Example 8 terpolymer).

Viscosities from stepped-shear experiments are listed in Tables 3 and 4 for all terpolymer examples. Differences between viscosities reflect the effects of initiator species, monomer composition, and molecular weight on the viscosity of the resulting polymer.

In particular, it is noted that viscosity decreases with increasing caprolactone content (comparison of Examples 10, 11, and 8) and also with increasing ratio of lactide to glycolide (comparison of Example 9 to Example 10).

Further, it is to be noted that the terpolymer made from L-lactide (Example 12) was found to be amorphous in nature (lacking any melting endotherms by DSC analysis) and had a relatively low viscosity which was consistent with a similar terpolymer prepared using DL-lactide (Example 8).

Finally, molecular weight effects on viscosity are also observed between terpolymers of Examples 1 and 11. Comparison between these samples shows that viscosity increases from 655 poise to 1,720 poise as the polymer molecular weight is raised from about 4,800 to 9,900 daltons.

TABLE 3

Steady-state viscosities of high molecular weight terpolymer examples. Actual terpolymer compositions are mole ratios of lactide (L), glycolide (G), and caprolactone (C) as determined by NMR.

| Example No. | Initiator | terpolymer composition, L:G:C mole ratio | Weight-average molecular weight, kD | Steady-state viscosity, Poise |
| --- | --- | --- | --- | --- |
| 1 | 1-Dodecanol | 27:19:54 | 9.9 | 1720 |
| 2 | Ethyl Glycolate | 27:21:52 | 10.0 | 6510 |
| 3 | Oleyl Alcohol | 27:19:54 | 11.0 | 1710 |
| 4 | Glycerol | 27:19:54 | 7.6 | 3360 |
| 5 | Methoxy PEG 350 | 28:19:53 | 9.3 | 1940 |
| 6 | Monolauryl-PEG 400 | 30:20:50 | 16.0 | 8570 |
| 7 | 1-Ethyl-2-Hexanol | 28:19:53 | 11.0 | 6330 |

TABLE 4

Steady-state viscosities of low molecular weight terpolymer examples. Actual terpolymer compositions are mole ratios of lactide (L), glycolide (G), and caprolactone (C) as determined by NMR.

| Example No. | Initiator | terpolymer composition, L:G:C mole ratio | Weight-average molecular weight, kD | Steady-state viscosity, Poise |
| --- | --- | --- | --- | --- |
| 8 | 1-Dodecanol | 16:26:58 | 4.8 | 282 |
| 9 | 1-Dodecanol | 44:28:28 | 4.5 | 20540 |
| 10 | 1-Dodecanol | 50:20:30 | 4.5 | 13300 |
| 11 | 1-Dodecanol | 31:20:49 | 4.8 | 655 |
| 12 | 1-Dodecanol | 15:29:56 | 5.1 | 455 |
| 13 | Oleyl Alcohol | 23:26:51 | 4.7 | 316 |
| 14 | Ethyl Glycolate | 16:31:53 | 5.7 | 2639 |

Example 16

Terpolymer Admixtures Comprising Small Quantities of Additives or Plasticizers

Figure 4:
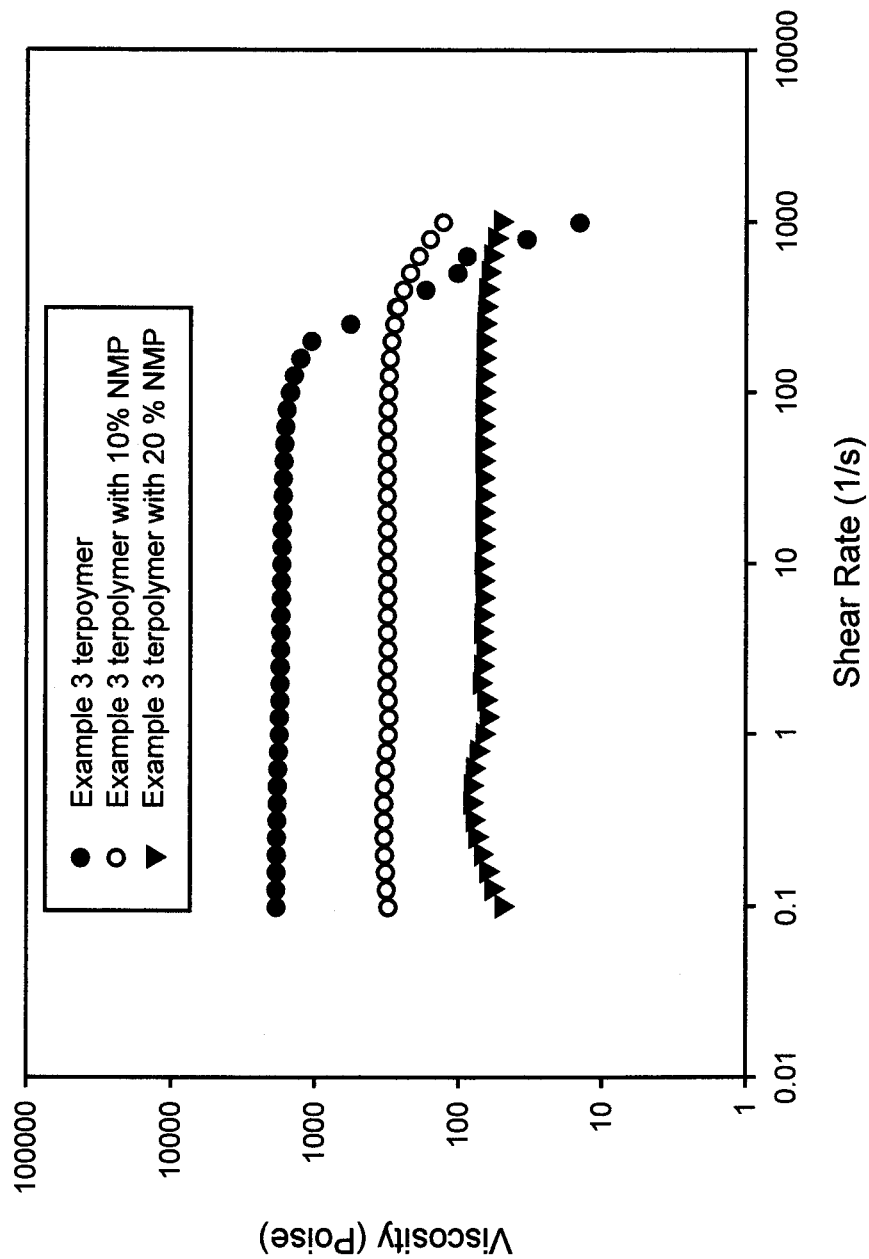
FIG. 4 is a graph of viscosity (poise) versus shear rate (sec$^{-1}$) data for various admixtures of Example 3 terpolymer diluted with 0%, 10%, 20% (w/w) N-methyl pyrrolidone (NMP).
Figure 5:
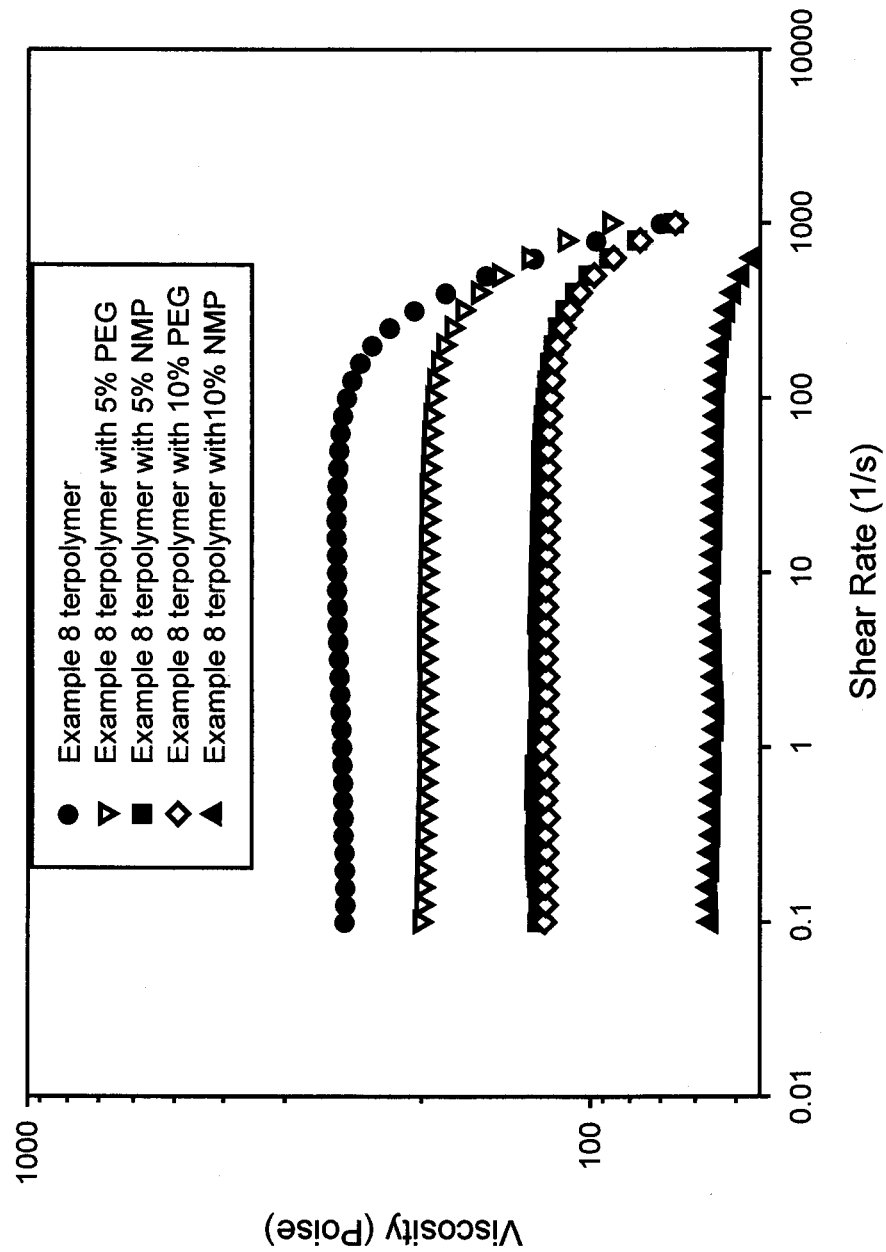
FIG. 5 is a graph of viscosity (poise) versus shear rate (sec$^-$) data for various admixtures of Example 8 terpolymer diluted with 0%, 5%, 10% (w/w) N-methyl pyrrolidone (NMP) and PEG-400.
Figure 6:
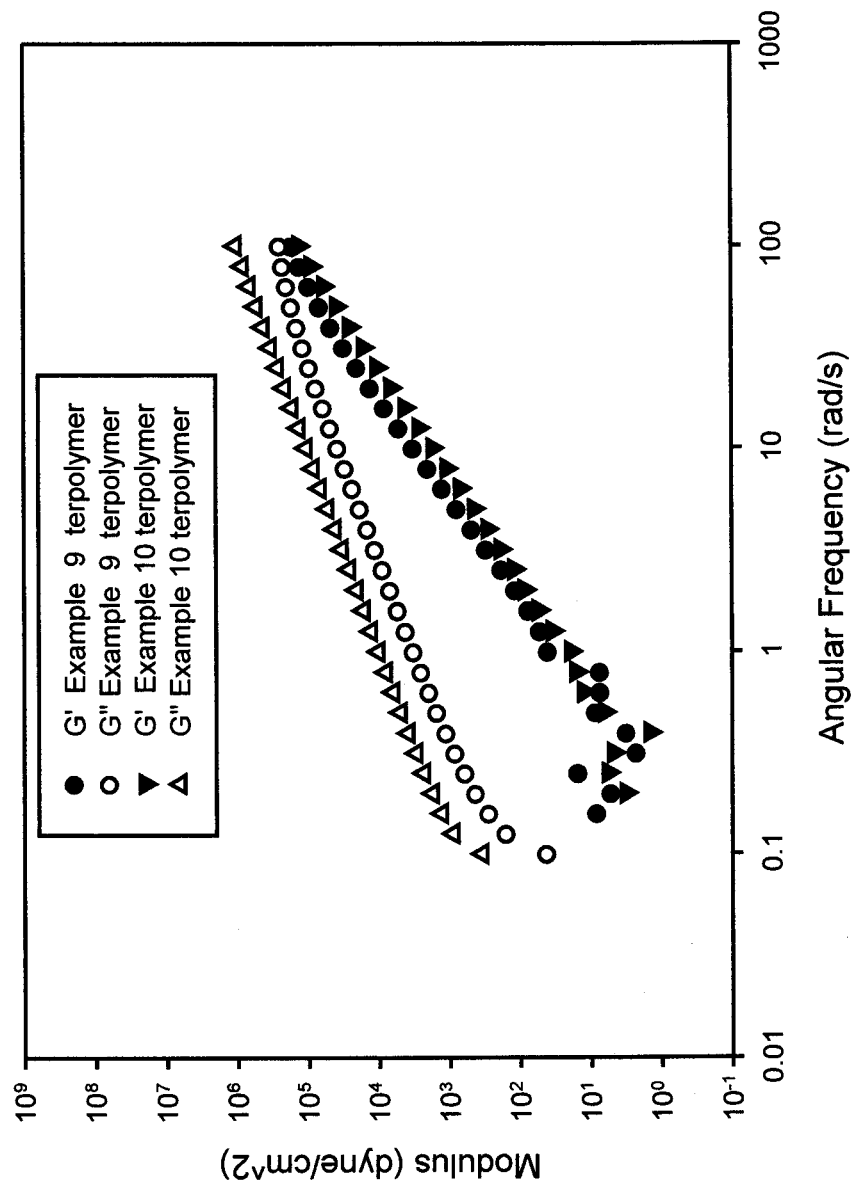
FIG. 6 is a graph of storage (G') and loss moduli (G") of select terpolymers determined using oscillatory rheology.

Terpolymer admixtures were prepared by mixing with various additives in a 20-mL scintillation vial to give a total of 2-grams per sample. Each admixture was blended by hand using a spatula to fully incorporate and distribute the additive in each terpolymer sample. As shown in FIGS. 4 and 5, diluting the terpolymers described in examples 3 and 8 with small quantities of either NMP or PEG-400 resulted in a significant decrease in viscosity. Table 5 shows the change in viscosity of several terpolymers following dilution with varying levels of NMP.

TABLE 5

Viscosity of polymers with added plasticizer NMP

| Example (polymer) | Plasticizer | Composition, wt % polymer | Steady state viscosity, poise |
| --- | --- | --- | --- |
| 3 | (none) | 100% | 1,710 |
| 3 | NMP | 90% | 300 |
| 3 | NMP | 80% | 70 |
| 4 | (none) | 100% | 3,360 |
| 4 | NMP | 90% | 350 |
| 4 | NMP | 80% | 95 |
| 2 | (none) | 100% | 6,510 |
| 2 | NMP | 80% | 80 |

Example 17

Brookfield Viscosities

Comparison of Brookfield (Rotational Viscosity) and Stepped-Shear Viscosities Between Terpolymer Examples and PLG Controls The terpolymer from Example 8 was used to compare viscosity results between parallel plate measurements (AR 2000 rheometer) and a Brookfield rotational viscometer. The sample was prepared by adding 10 wt % NMP to a portion of Example 8 terpolymer resulting in a composition comprising 90% polymer in NMP. For comparison purposes, solutions of two 75:25 poly(DL-lactide-co-glycolide) (PLG) copolymers (3E copolymer and a 4E copolymer) were prepared by diluting each PLG copolymer with 60 wt % NMP. Correspondingly, these samples reflect a composition comprising only 40% polymer in NMP. Stepped-shear and Brookfield viscosity measurements were performed on samples and the corresponding steady-state and Brookfield viscosities are reported as indicated in Table 6. Results confirm that viscosities are consistent between methods and demonstrate that terpolymer formulations having viscosity suitable for parenteral injection can be prepared.

TABLE 6

Comparison of steady-state viscosities to Brookfield Viscometer Values.

| Sample description (% polymer in Additive) | Viscosity (Poise) | Rotational viscosity (Brookfield) (Poise) |
| --- | --- | --- |
| Example 8 terpolymer (90% polymer in NMP) | 60.2 | 80.0 |
| 7525 DLG, 3E (40% polymer in NMP) | 32.2 | 24.6 |
| 75:25 DLG, 4E (40% polymer in NMP) | 88.4 | np | np—not performed.

Example 18

Terpolymer Admixtures Comprising Additives (Physical Attributes, Changes)

Terpolymer admixtures were prepared as described in Example 16 using other additives as is described in Table 7. Choice of terpolymer, additive, and additive composition may affect the texture (or tackiness) of the admixture from being a highly sticky material to a moderately sticky material (tacky) to a material with little or no tackiness (as indicated using the term "dry"). In addition to texture, the physical form of the admixture may change from a high- or low-viscosity material, to semi-solid, to a crumbly solid or a moldable (cohesive) solid or semi-solid. The additives identified in Table 7 were obtained from commercial vendors; chitosan (Protosan UP G213) was purchased from NovaMatrix (Norway).

TABLE 7

Physical attributes of various terpolymer admixtures.

| Polymer ID | Additive ID | % Additive | Texture | Physical Form | Other Observations |
|---|---|---|---|---|---|
| Example 1 | Hydroxyapatite | 10 | sticky | Viscous | — |
| Example 1 | Hydroxyapatite | 25 | tacky | Highly Viscous | — |
| Example 1 | Hydroxyapatite | 50 | tacky | semi-solid | — |
| Example 8 | Hydroxyapatite | 10 | sticky | Viscous | — |
| Example 8 | Hydroxyapatite | 25 | tacky | Highly Viscous | — |
| Example 8 | Hydroxyapatite | 50 | tacky | semi-solid | — |
| Example 8 | Hydroxyapatite | 75 | dry | solid | Crumbly material |
| Example 1 | β-tricalcium phosphate | 10 | no change | no change | — |
| Example 1 | β-tricalcium phosphate | 25 | sticky | thin | — |
| Example 1 | β-tricalcium phosphate | 50 | sticky | semi-solid | — |
| Example 1 | β-tricalcium phosphate | 75 | dry | semi-solid | moldable |
| Example 8 | β-tricalcium phosphate | 10 | sticky | thin | — |
| Example 8 | β-tricalcium phosphate | 25 | sticky | viscous | — |
| Example 8 | β-tricalcium phosphate | 50 | sticky | semi-solid | — |
| Example 8 | β-tricalcium phosphate | 75 | dry | solid | moldable |
| Example 1 | Calcium Carbonate | 10 | no change | no change | — |
| Example 1 | Calcium Carbonate | 10 | no change | no change | — |
| Example 8 | PEG 400 | 10 | sticky | viscous | — |
| Example 8 | PEG 400 | 25 | sticky | slightly viscous | — |
| Example 8 | PEG 400 | 50 | sticky | thin | — |
| Example 8 | PEG 400 | 75 | sticky | flowable | — |
| Example 8 | Pluronic F-127 in distilled water (20%) | 40 | sticky | viscous | transparent to white |
| Example 8 | Pluronic F-127 (100%) | 40 | sticky | slightly viscous | not well dispersed |
| Example 8 | Chitosan G 213 | 10 | very sticky | viscous | transparent to white |
| Example 8 | Chitosan G 213 | 25 | sticky | thick | — |
| Example 8 | Chitosan G 213 | 50 | tacky | semi-solid | — |
| Example 8 | Chitosan G 213 | 65 | dry | solid | moldable |

Example 19

Oscillatory Rheology

Results from oscillatory rheology measurements on Example 9 are representative of those of all terpolymers which exhibit a G″ that is greater than G′, results that are consistent with liquid-like (viscous) materials.

Example 20

Loading and Release of Low Molecular Weight Model Hydrophilic Compound (Methylene Blue)

Three different samples of a methylene blue-loaded terpolymer were prepared as follows. A 0.5 gram portion of methylene blue tri-hydrate (Fisher Scientific, Fairlawn N.J.) was dissolved in 5 grams of ethanol. Next, a 1-gram sample of Example 1 terpolymer was weighed into a 20-mL scintillation vial. Then 200 mg of the ethanolic methylene blue solution was added to the vial and was thoroughly mixed by hand into the terpolymer. The residual ethanol was allowed to evaporate to the polymer for at least 16 hours leaving a formulation comprising 20 mg methylene blue in 1 gram polymer (approx 2 wt % loading methylene blue in polymer). One of these samples was diluted with 10% by weight NMP by adding and thoroughly incorporating 0.25 g NMP into the sample. Similarly, a second sample was diluted with 10% by weight ethanol by adding and thoroughly incorporating 0.25 g ethanol into the sample.

The same sample preparation methodology was repeated using Example 8 terpolymer.

Figure 7:
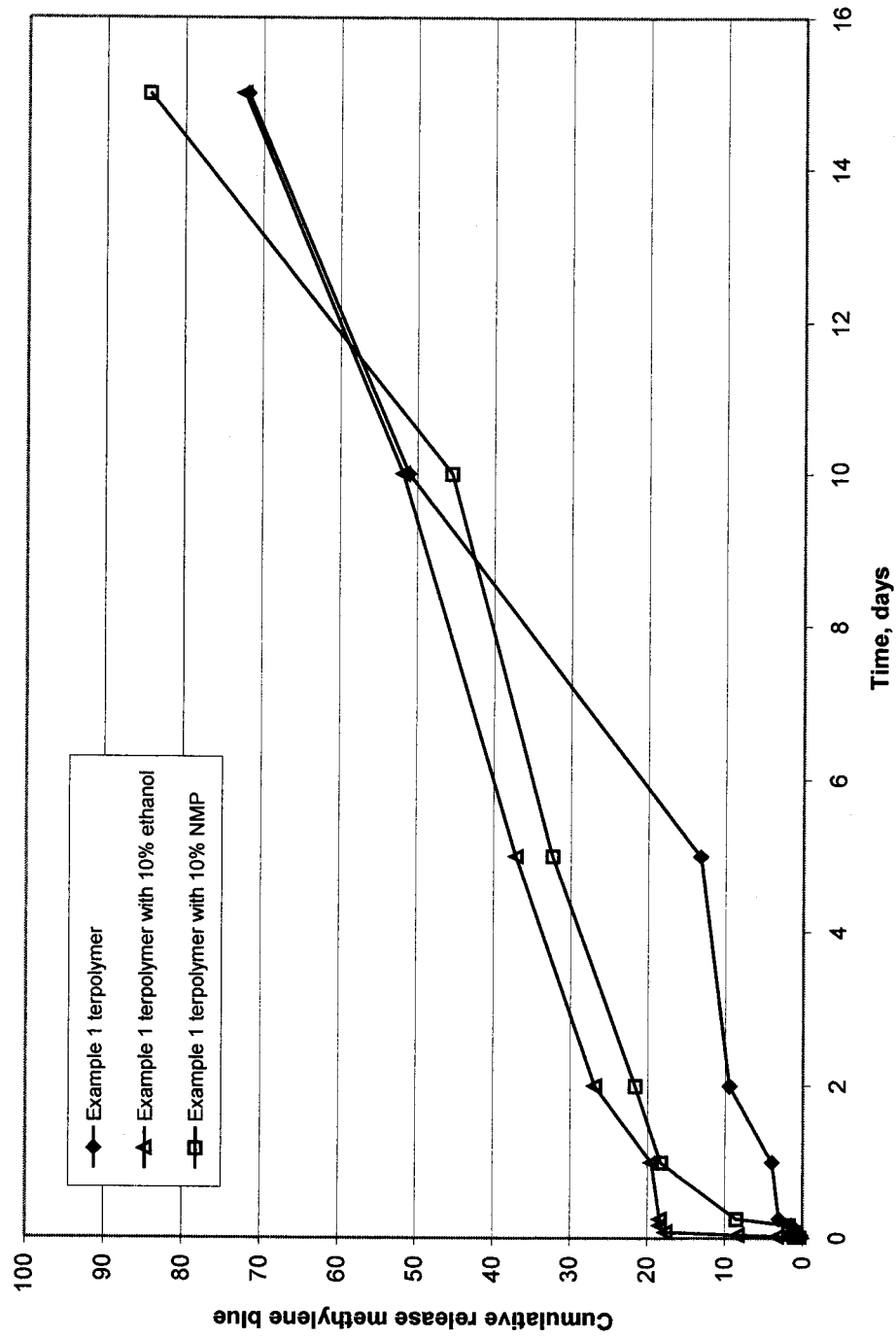
FIG. 7 is a graph showing the in vitro release of a model hydrophilic small-molecule compound, methylene blue, from 2%-loaded composition of Example 1 terpolymer. Compositions tested included 2% methylene blue in the terpolymer (methylene blue in the neat polymer) and then formulations of 2% methylene blue in terpolymer admixed with 10% (by weight) ethanol or NMP.
Figure 8:
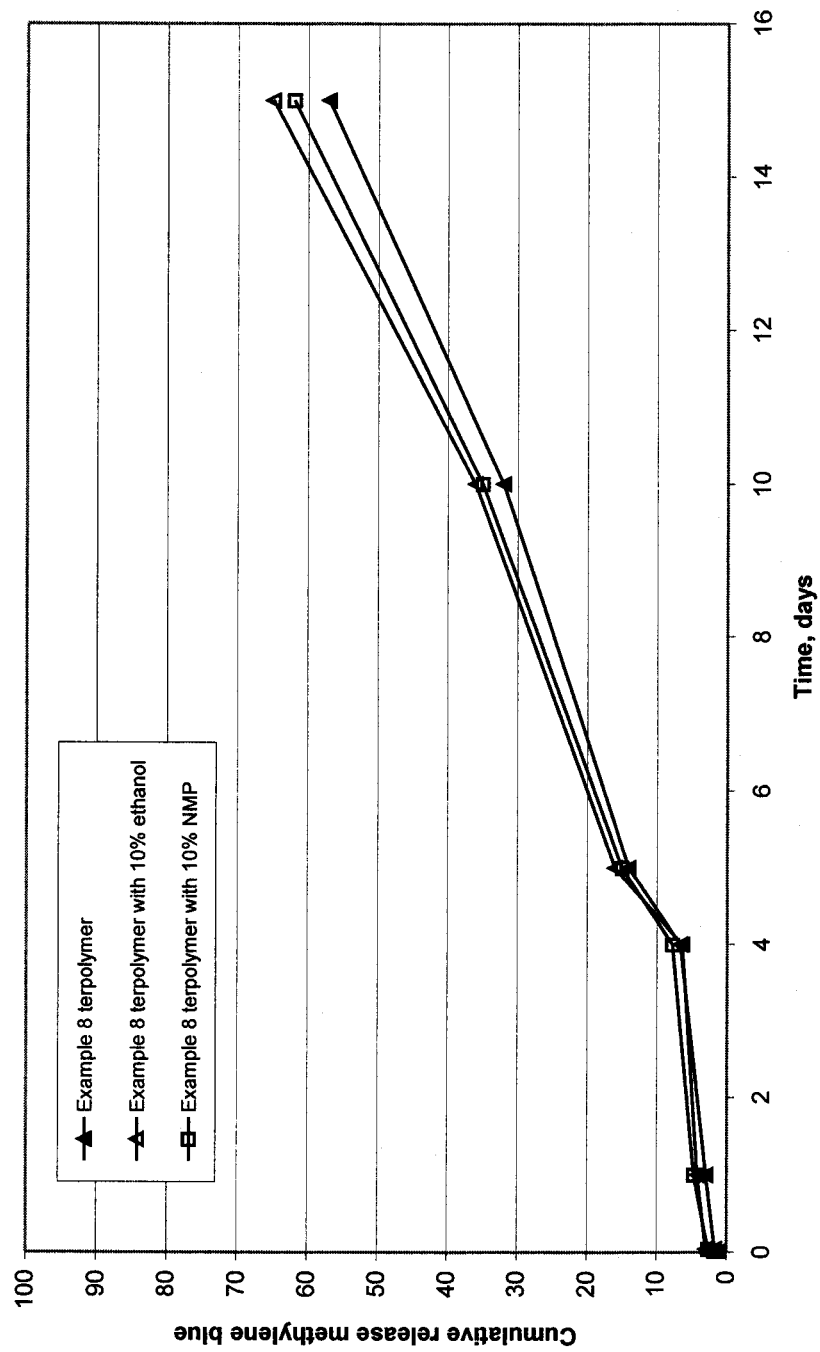
FIG. 8 is a graph showing the in vitro release of a model hydrophilic small-molecule compound, methylene blue, from 2%-loaded Example 8 terpolymer and from admixtures containing 10% (w/w) NMP or ethanol.

In vitro release studies were conducted on these formulations as follows. An accurately-weighed portion of the methylene blue composition (about 75 to 100 mg) was weighed into a 20 mL scintillation vial and 20 mL of phosphate-buffered saline, pH 7.4 (PBS) was added. The vial was placed in an incubator whose temperature was maintained at 37° C. At the appropriate time point, the vials are mixed by inversion and 0.5 mL of buffer was removed from the vial. The vial was placed back into the incubator until the next time point. The buffer containing released methylene blue was assayed for methylene blue by HPLC (detection by UV at 254 nm). Cumulative released methylene blue was determined. Cumulative release curves are shown in FIGS. 7 and 8 for the formulations prepared from Example 1 and Example 8 terpolymers, respectively.

Neat terpolymer formulations are found to provide prolonged release of methylene blue, a highly hydrophilic model compound, over days to weeks with little or no initial burst in release during the early timepoints studied (initial burst). Terpolymer formulations comprising additional small levels of additives such as ethanol or NMP were prepared as previously described. The addition of these additives small and variable effects on initial burst and overall release profiles. In both terpolymer compositions, however, cumulative release at the Day 1 timepoint (initial burst) remained at or below about 20%. In the case of Example 8 terpolymer, the initial burst was not at all affected by the presence of these additives.

Example 21

Loading and Release of Model Peptide (Goserelin) in a Terpolymer Composition

A 10% (by weight) blend of goserelin (Genzyme Pharmaceuticals) in terpolymer was prepared by adding 110 mg goserelin to a 20-mL scintillation vial containing 1 gram of Example 8 terpolymer. The contents were thoroughly mixed by hand using a spatula.

Drug content of the mixture was analyzed by transferring a known quantity (20-30 mg) of the blend into a 25-mL volumetric flask. To this flask, 5-mL glacial acetic acid was added and the sample was allowed to dissolve. Once the sample had dissolved, the flask was filled to volume using PBS and thoroughly mixed. The resulting solution was then filtered through a 0.45 μm syringe filter before analysis by HPCL using UV detection at 220 nm. The theoretical goserelin content of this composition was 10 wt % goserelin; the actual content as determined by HPLC was 9.9 wt % goserelin in the polymer blend.

Figure 9:
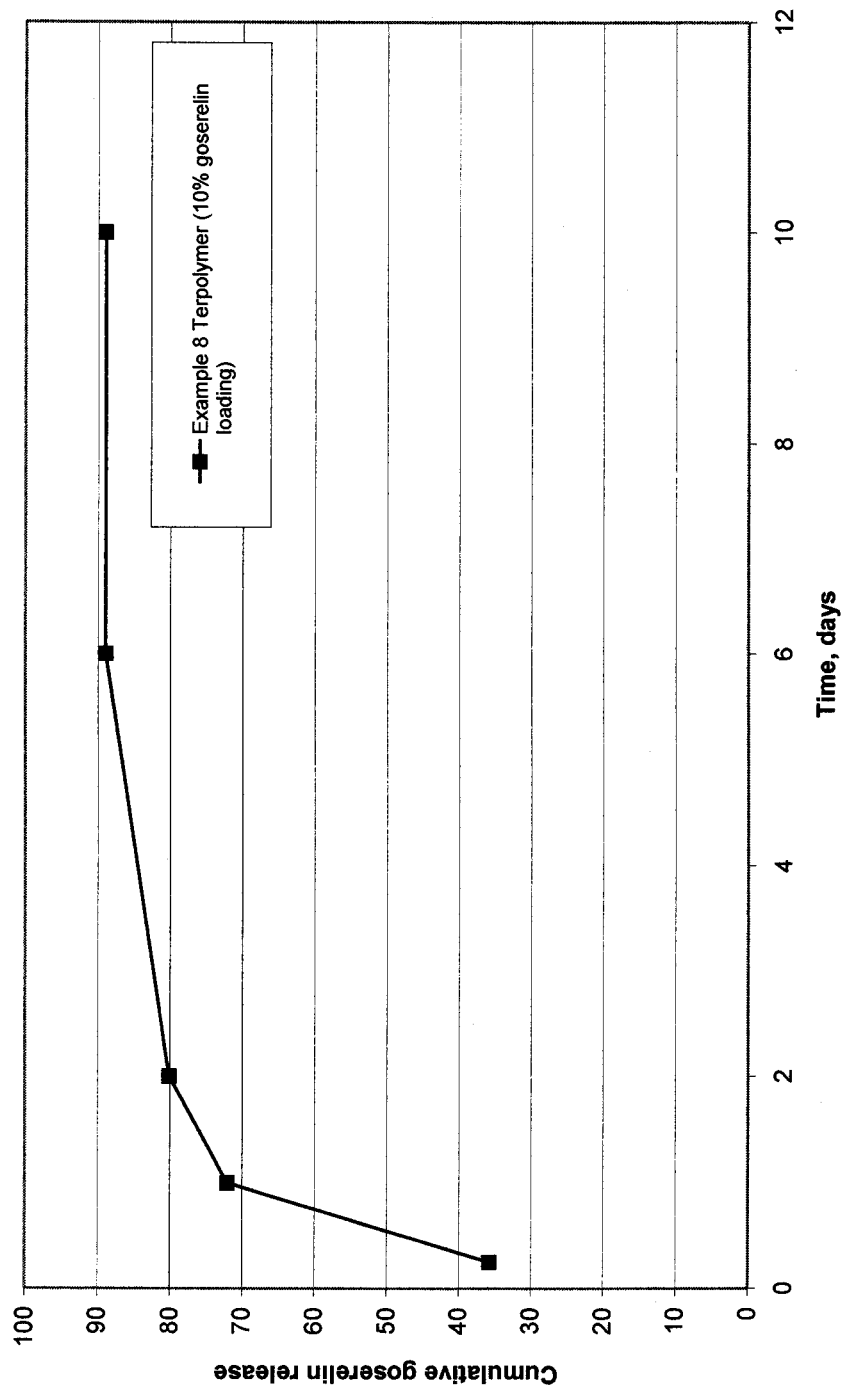
FIG. 9 is a graph showing the in vitro release of a model peptide, goserelin, from a 10%-loaded formulation of Example 8 terpolymer. Release studies were performed on a 50-mg sample that was spread out across (approximately) a 15 square mm area.

In vitro release measurements were conducted by carefully preparing a sample of known weight and surface area as follows. An accurately weight sample of the goserelin formulation (approximately 50 mg sample) was added to the center of a 20×20 mm glass microscope cover-slip. The goserelin formulation was spread out across an area measuring approximately 15×15 mm. The final weight of the formulation was accurately determined (approximately 50 mg). The cover-slip was then carefully placed (sample facing upwards) at the bottom of a 30-mL glass vial. Then 20-mL of an in vitro release buffer (PBS) was slowly added to the vial making sure the sample remains facing upwards. The vial was placed in an incubator whose temperature was maintained at 37° C. At the selected time intervals, the vial contents are carefully mixed by gentle swirling and then a 10-mL sample was removed from the vial and an equivalent amount of fresh PBS was added back into the vial. The vial was placed back into the incubator until the next time point. The sample was assayed for goserelin using a HPLC method (using UV detection at 220 nm). Cumulative released goserelin was determined. The cumulative goserelin release curve is shown in FIG. 9.

Example 22

Loading and Release of Model Local Anesthetic Bupivacaine Base in a Terpolymer Composition Bupivacaine hydrochloride was purchased from Sigma-Aldrich (melting temperature 255° C.). Bupivacaine hydrochloride was used to prepare bupivacaine base as follows. About 10 grams of bupivacaine hydrochloride was placed in a 500-mL Erlenmeyer flask containing 300-mL deionized water. The solution was stirred at 50° C. until the bupivacaine hydrochloride dissolved. Once dissolved, 6M ammonium hydroxide was slowly added until the pH of the mixture reached 9.5. The solution was stirred for an additional 10 minutes and the pH adjusted to maintain pH in the range of 9.5 to 10. The flask was then cooled resulting in the precipitation of the bupivacaine base. The precipitate was collected on a filter funnel and then rinsed with 500 mL of cold, deionized water. The bupivacaine base was then transferred to a 1-L lyophilizer flask. The product was suspended in 100-mL deionized water, frozen, then lyophilized to obtain a dry powder. Yield of the bupivacaine base is typically 7-8 grams total. Melting temperature of the product as obtained is 106° C. (literature value of 107° C.).

In this example, a 1-gram sample of Example 8 terpolymer was placed in a 20-mL scintillation vial along with 660 mg of bupivacaine base. The sample was thoroughly mixed by hand using a spatula. A second sample was prepared in a similar manner using the Example 1 terpolymer.

Drug content of the formulation was analyzed by transferring a known quantity (20-30 mg) of the composition into a 25-mL volumetric flask. To this flask, 5-mL glacial acetic acid was added and the sample was allowed to dissolve. Once the sample had dissolved, the flask was filled to volume using PBS and thoroughly mixed. The resulting solution was then filtered through a 0.45 μm syringe filter before analysis by HPCL using UV detection at 263 nm. The theoretical bupivacaine base content of these two compositions was 40 wt % bupivacaine; the actual content determined by HPLC was 40.0 wt % for the composition made from the polymer of Example 8 and 39.0 wt % for the composition made from the polymer of Example 1.

Figure 10:
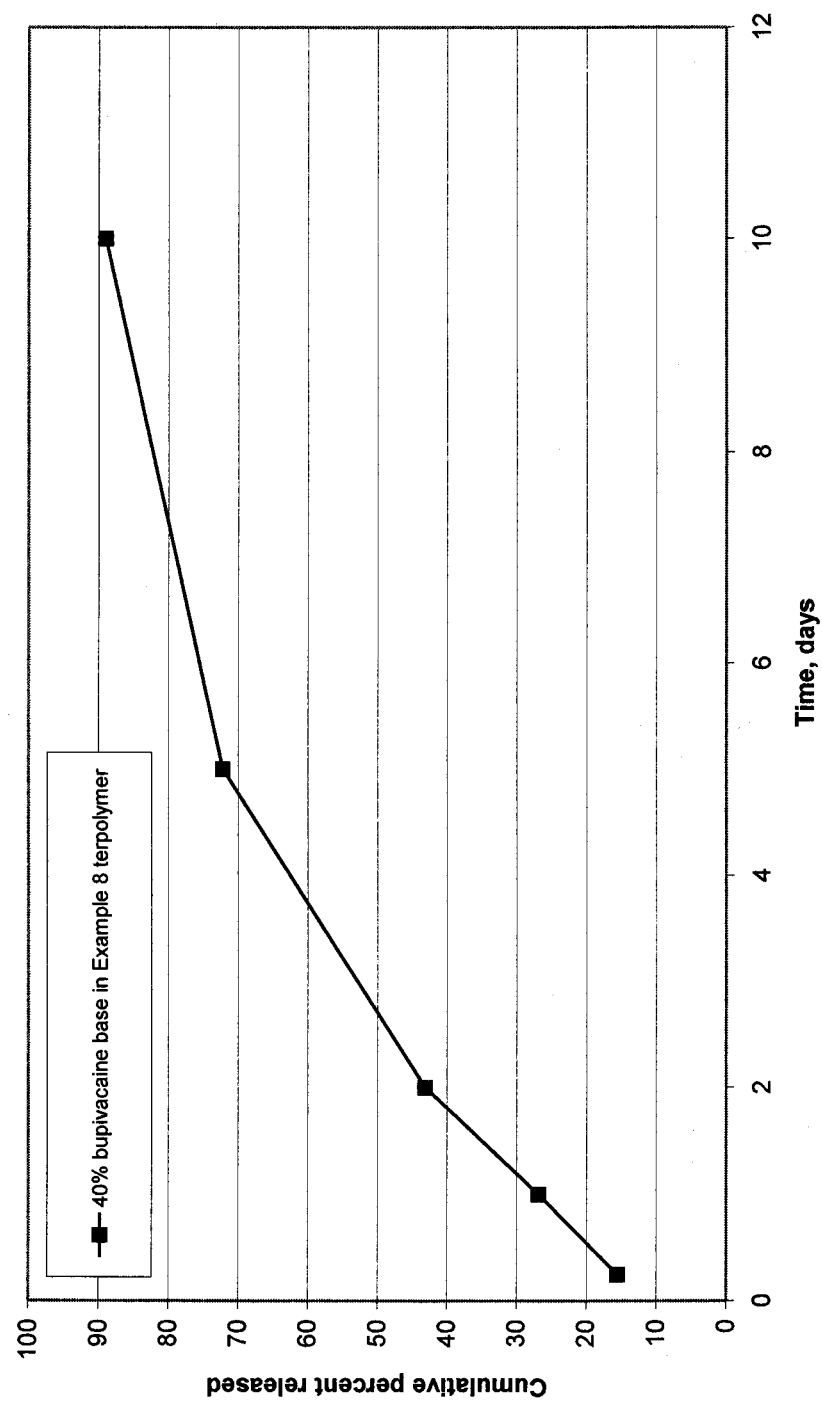
FIG. 10 is a graph showing the in vitro release of a bupivacaine base from a 40%-loaded formulation in Example 8 terpolymer. Release studies were performed on a 50-mg sample that was spread out across (approximately) a 20 square mm area.
Figure 11:
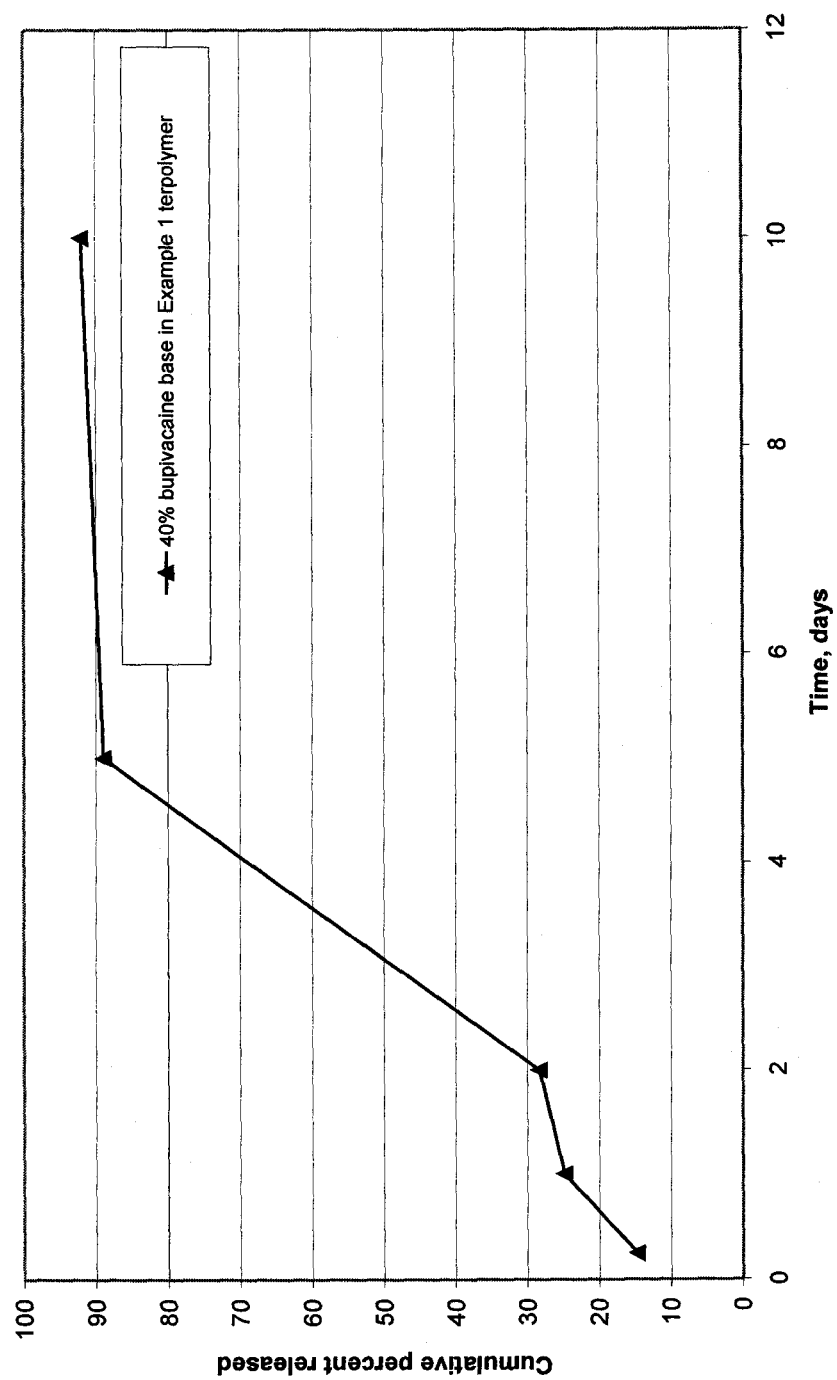
FIG. 11 is a graph showing the in vitro release of a bupivacaine base from a 40%-loaded formulation of Example 1 terpolymer. Release studies were performed on a 50-mg sample that was spread out across (approximately) a 20 square mm area.

In vitro release rate studies were carried out by spreading a 50-mg sample onto a 20 square cm glass microscope slide cover-slip. The sample was spread across the entire 20 square cm area of the cover-slip. The cover-slip was then carefully placed at the bottom of a 60-mL screw-cap vial and then 60-mL of PBS was added. Samples were stored in an incubator at 37° C. At the indicated time intervals, 20-mL of buffer was removed from the vial and a 20-mL portion of fresh buffer was replaced back into the vial. Bupivacaine base was analyzed by HPLC using UV detection at 263 nm. Cumulative percent release of bupivacaine was reported. Release rate profiles are shown in FIGS. 10 and 11 for the two compositions of this example.

Example 23

In Vitro Release of Bupivacaine Hydrochloride and Bupivacaine Base from Example 8 Terpolymer The formulation from Example 22 comprising bupivacaine base in Example 8 terpolymer was used in this study.

A second formulation was prepared in a similar manner using lyophilized portion of bupivacaine hydrochloride. Briefly, a 2-g sample of bupivacaine hydrochloride dissolved in 200 mL deionized water which was shell-frozen inside a 1-L lyophilization jar and then lyophilized to a dry powder.

Figure 12:
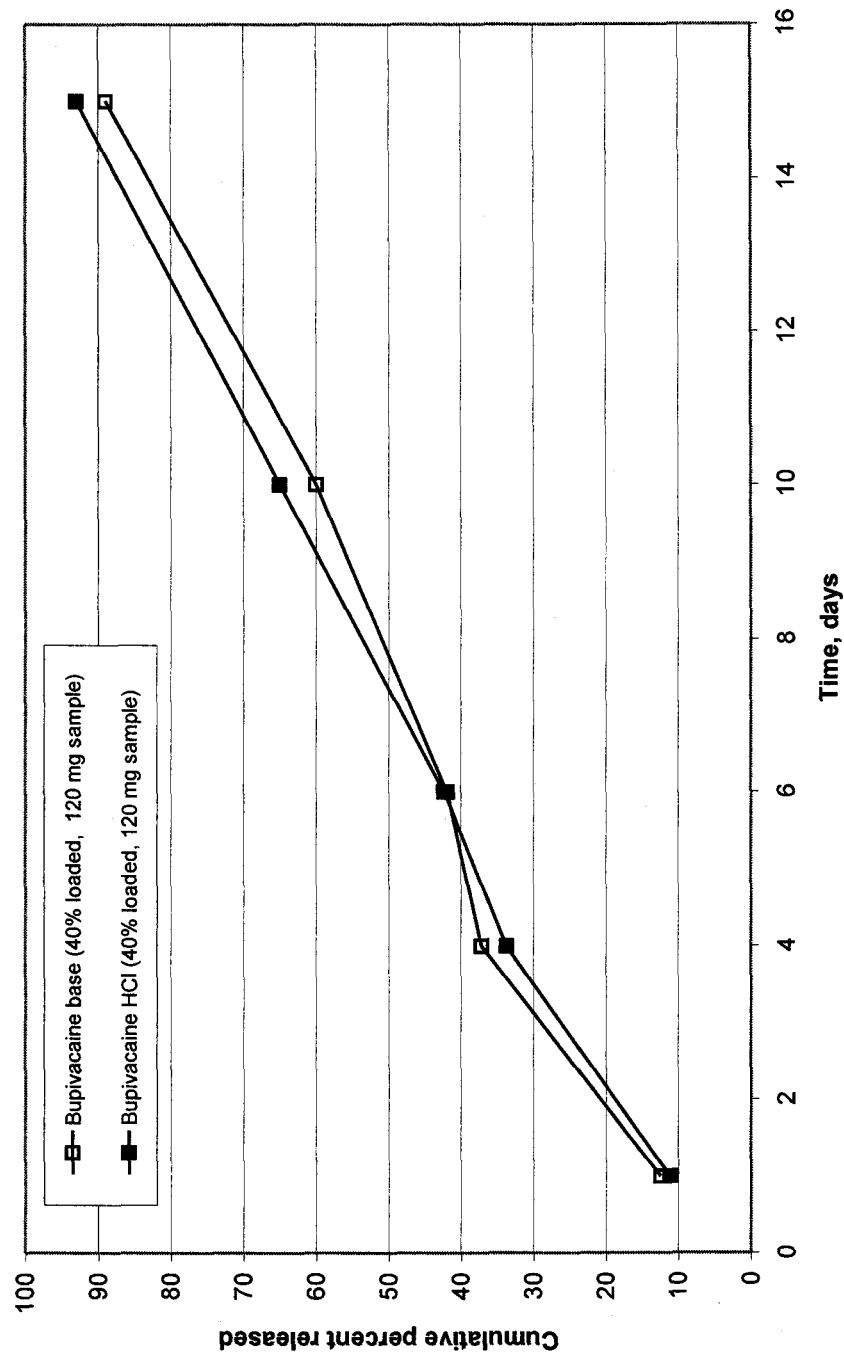
FIG. 12 is a graph showing the in vitro release of a bupivacaine base and bupivacaine hydrochloride from a 40%-loaded formulation of Example 8 terpolymer. Release studies were performed on 120 mg samples that were spread out across (approximately) a 20 square mm area.

A 40 wt % blend of bupivacaine hydrochloride in Example 8 terpolymer was prepared in a similar manner as described in Example 22. An in vitro release experiment was conducted as described in Example 22 using a 120-mg sample that was spread out across a 20 square mm area. Release profiles of bupivacaine base and hydrochloride are presented in FIG. 12.

Example 24

Polymeric Micelle from PEG-Terpolymer AB Block Copolymer

Polymer Synthesis. PEG-Terpolymer AB Block Copolymer: 213643 DLGCL 1-(mPEG 2000)-E A glass reactor equipped with a magnetic stir bar was charged with 8.5 grams (0.059 mol) of DL-lactide (Ortec, South Carolina), 10.2 grams (0.088 mol) of glycolide (Ortec, South Carolina), 16.6 grams (0.145 mol) of ε-caprolactone (Ortec, South Carolina) and 53.8 grams (0.027 mol) of methoxypoly(ethylene glycol) (MW=2000) (Sigma-Aldrich, Wisconsin). The reaction was purged with nitrogen and the contents melted at 140° C. after which 27 milligrams (0.066 mmol) of the catalyst stannous octoate (Sigma-Aldrich, Wisconsin) was added. The polymerization proceeded for 18 hours at 160° C. followed by a 2 hour vacuum strip at 28.5 in HG vacuum to remove un-reacted monomer. DL-lactide:glycolide:ε-caprolactone mole ratio=21:36:43; Mn=3,000 from proton NMR.

Micelle Preparation and Characterization

A dilute polymer solution was prepared by dissolving the PEG-terpolymer AB block copolymer in deionized water at a concentration of 0.5 mg/mL. The resulting solution was passed through a 0.1 micron Supor Acrodisc 25 mm syringe filter (Pall Life Sciences) to prepare the solution of polymeric micelles.

Figure 13:
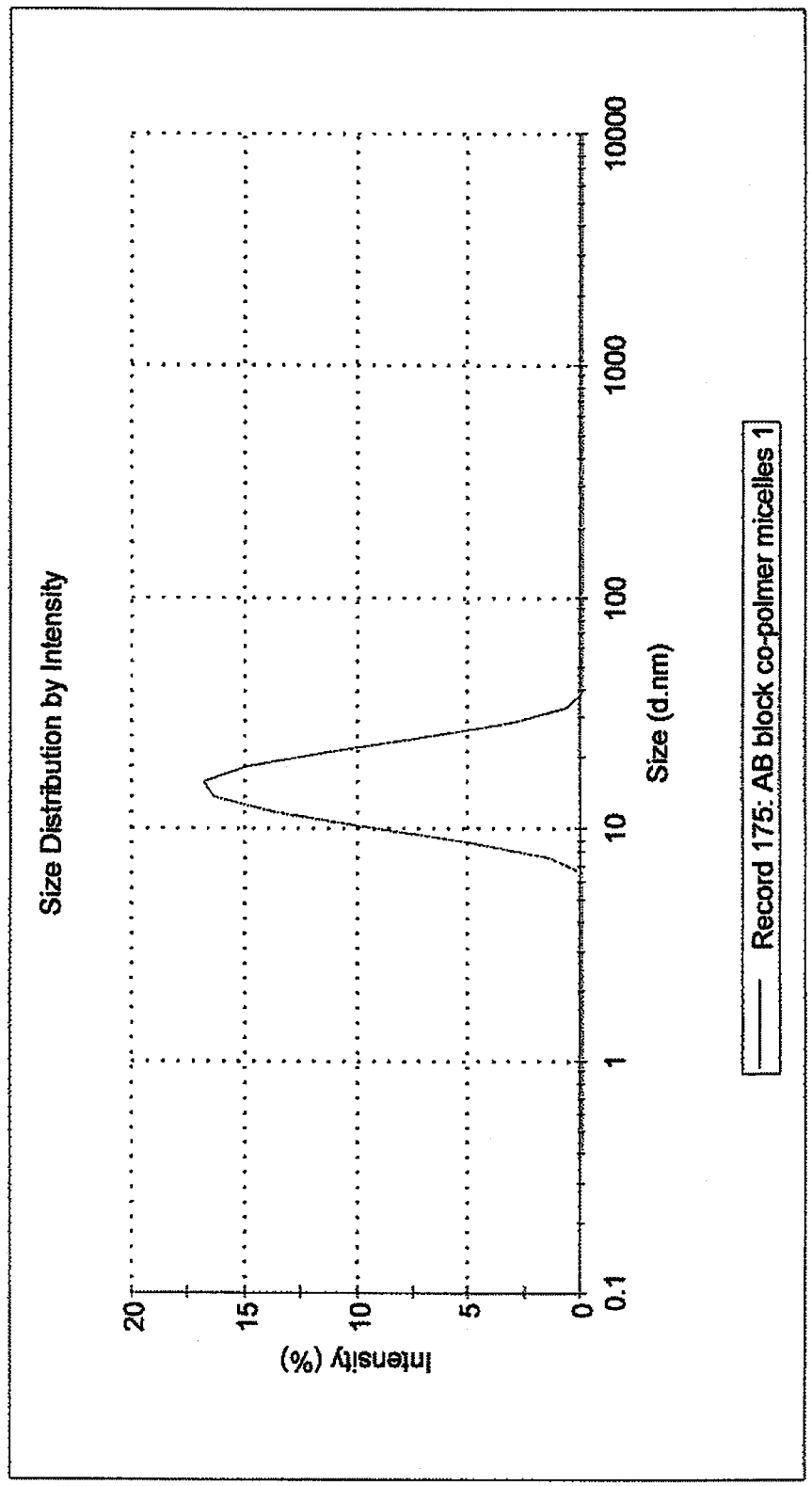
FIG. 13 is a graph of the particle size distribution of a polymeric micelle prepared from a PEG-terpolymer AB block copolymer by PCS.

The polymeric micelle solution was analyzed for particle size by photon correlation spectroscopy (PCS) using a Malvern ZetaSizer Nano-ZS (Model ZEN-3600) equipped with a 633 nm laser. The measured mean polymer micelle size was 14 nm and the size distribution plot is shown in FIG. 13.

It will be apparent to those skilled in the art that various modifications and variations can be made in the present invention without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A terpolymer composition, comprising: a terpolymer of lactide, glycolide, and caprolactone residues, wherein the terpolymer comprises an end group that is a residue of an initiator, wherein the initiator is selected from the group consisting of oleyl alcohol and 1-dodecanol; and wherein the amount of lactide residue in the terpolymer is from 10 to 31 mole percent, the amount of glycolide in the terpolymer is from 10 to 40 percent, and the amount of caprolactone is at least 49 mole percent; wherein the terpolymer has a Mw equal to or less than 11,000 Daltons wherein the terpolymer exhibits a steady-state viscosity of less than or equal to 1720 poise when measured at room temperature.

2. The composition of claim 1, wherein the amount of lactide residue in the terpolymer is 16 mole percent, the amount of glycolide residue is 26 mole percent, and the amount of caprolactone residue is 58 mole percent.

3. The composition of claim 1, wherein the terpolymer has a Tg of less than 20° C.

4. The composition of claim 1, further comprising a bioactive agent.

5. The composition of claim 4, wherein the bioactive agent comprises a drug, a peptide, a protein, an antibody or fragment thereof, a nucleic acid, or imaging agent.

6. The composition of claim 1, further comprising a plasticizer.

7. The composition of claim 1, further comprising an agent, surfactant, excipient, or additive.

8. The composition of claim 1, further comprising an aqueous diluent.

* * * * *